US009132142B2

(12) United States Patent
Morrow et al.

(10) Patent No.: US 9,132,142 B2
(45) Date of Patent: Sep. 15, 2015

(54) USE OF SECRETOR, LEWIS AND SIALYL ANTIGEN LEVELS IN CLINICAL SAMPLES AS PREDICTORS OF RISK FOR DISEASE

(71) Applicant: Children's Hospital Medical Center, Cincinnati, OH (US)

(72) Inventors: Ardythe L. Morrow, Cincinnati, OH (US); David S. Newburg, Newtonville, MA (US); Guillermo M. Ruiz-Palacios, Mexico City (MX)

(73) Assignees: The General Hospital Corporation, Boston, MA (US); Instituto Nacional de Ciencias Medicas Y Nutricion, Mexico City (MX); Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 14/044,328

(22) Filed: Oct. 2, 2013

(65) Prior Publication Data

US 2014/0140970 A1 May 22, 2014

Related U.S. Application Data

(60) Division of application No. 13/006,795, filed on Jan. 14, 2011, now Pat. No. 8,574,850, which is a continuation of application No. 12/205,089, filed on Sep. 5, 2008, now Pat. No. 7,871,785.

(60) Provisional application No. 60/970,902, filed on Sep. 7, 2007.

(51) Int. Cl.
| | |
|---|---|
| *A61K 45/00* | (2006.01) |
| *A61K 31/7028* | (2006.01) |
| *G01N 33/68* | (2006.01) |
| *G01N 33/80* | (2006.01) |
| *A61K 31/702* | (2006.01) |
| *A61K 31/715* | (2006.01) |
| *A61K 35/741* | (2015.01) |
| *A61K 35/745* | (2015.01) |
| *A61K 35/747* | (2015.01) |
| *A61K 36/06* | (2006.01) |
| *A61K 38/02* | (2006.01) |
| *A61K 45/06* | (2006.01) |

(52) U.S. Cl.
CPC ........... *A61K 31/7028* (2013.01); *A61K 31/702* (2013.01); *A61K 31/715* (2013.01); *A61K 35/741* (2013.01); *A61K 35/745* (2013.01); *A61K 35/747* (2013.01); *A61K 36/06* (2013.01); *A61K 38/02* (2013.01); *A61K 45/06* (2013.01); *G01N 33/6893* (2013.01); *G01N 33/80* (2013.01); *G01N 2800/067* (2013.01)

(58) Field of Classification Search
None
See application file for complete search history.

(56) References Cited

U.S. PATENT DOCUMENTS

| | | | |
|---|---|---|---|
| 3,681,373 A * | 8/1972 | Adams et al. .............. 548/264.8 |
| 5,470,843 A | 11/1995 | Stahl et al. |
| 5,474,986 A | 12/1995 | Magnusson et al. |
| 5,484,773 A | 1/1996 | Heerze et al. |
| 5,576,300 A | 11/1996 | Mukerji et al. |
| 5,635,606 A | 6/1997 | Heerze et al. |
| 5,700,671 A | 12/1997 | Prieto et al. |
| 5,892,070 A | 4/1999 | Prieto et al. |
| 5,919,913 A | 7/1999 | Nuyens et al. |
| 6,045,854 A | 4/2000 | Prieto et al. |
| 6,126,961 A | 10/2000 | Kross |
| 6,132,710 A | 10/2000 | Panigrahi et al. |
| 6,146,670 A | 11/2000 | Prieto et al. |
| 6,204,431 B1 | 3/2001 | Prieto et al. |
| 6,291,435 B1 | 9/2001 | Yanmaele et al. |
| 7,871,785 B2 | 1/2011 | Morrow et al. |
| 7,893,041 B2 | 2/2011 | Morrow et al. |
| 8,314,061 B2 | 11/2012 | Morrow et al. |
| 8,574,850 B2 | 11/2013 | Morrow et al. |
| 2002/0019991 A1 | 2/2002 | Prieto et al. |
| 2002/0058313 A1 | 5/2002 | Renkonen et al. |
| 2006/0040893 A1 | 2/2006 | Harn et al. |
| 2007/0275881 A1 | 11/2007 | Morrow et al. |
| 2011/0207659 A1 | 8/2011 | Morrow et al. |
| 2012/0202753 A1 | 8/2012 | Morrow et al. |
| 2015/0079055 A1 | 3/2015 | Morrow et al. |

FOREIGN PATENT DOCUMENTS

| | | |
|---|---|---|
| EP | 0870841 A1 | 10/1998 |
| EP | 1199364 A2 | 4/2002 |
| EP | 1199364 A3 | 3/2004 |

(Continued)

OTHER PUBLICATIONS

Newburg et al.(Advanced Exp Med Biol 2004 vol. 554, p. 457-461).*
Morrow et al. Human milk oligosaccharide blodd group epitopes and innate immune protection against *Campylobacter* and Calicivirus diarrhea in breastfed infants Edited by Pickering et al.. Kluwer Academic/Plenum Publishers, p. 443-446, 2004.*
Morrow (II) et al. J. Nutr. 135: 1304-1307, 2005.*
Parashar et al. (Arch Pediatr Adolesc Med. 1998 vol. 152, p. 47-51).*
Rivero et al. Advances in Experimental Medicine and Biology 2005 vol. 569, p. 186-187.*
Supplementary European Search Report for Application No. EP 08799226.9 mailed Dec. 21, 2010.
Office Action for Application No. EP 08799226.9 mailed May 24, 2012.

(Continued)

*Primary Examiner* — Jacob Cheu
(74) *Attorney, Agent, or Firm* — Wolf, Greenfield & Sacks, P.C.

(57) ABSTRACT

An individual at risk for necrotizing enterocolitis and related disorders can be identified by measuring the level of at least one secretor antigen in a biological sample from the individual and comparing the measured level of the at least one secretor antigen to a predetermined value or a predetermined range of values. Among the secretor antigens which can be measured are: the H-1, H-2, Lewis[b] and Lewis[y] antigens and derivatives thereof (e.g., a sialylated form of Lewis a, Lewis x, Lewis b, Lewis y; H-1, H-2, Lewis a, Lewis x, Lewis b or Lewis y).

26 Claims, 8 Drawing Sheets

(56) References Cited

FOREIGN PATENT DOCUMENTS

| | | |
|---|---|---|
| JP | 2002-218996 A | 8/2002 |
| JP | 2004-528529 A | 9/2004 |
| JP | 2006-506329 A | 2/2006 |
| WO | WO 92/18610 A2 | 10/1992 |
| WO | WO 94/18986 A1 | 9/1994 |
| WO | WO 95/24495 A1 | 9/1995 |
| WO | WO 99/31224 A2 | 6/1999 |
| WO | WO 99/56754 | 11/1999 |
| WO | WO 02/43578 A2 | 6/2002 |
| WO | WO 2004/041291 A1 | 5/2004 |
| WO | WO 2005/055944 A2 | 6/2005 |
| WO | WO 2006/017859 A2 | 2/2006 |
| WO | WO 2007/087468 A2 | 8/2007 |
| WO | WO 2007/090894 A1 | 8/2007 |
| WO | WO 2009/077352 A1 | 6/2009 |

OTHER PUBLICATIONS

Blackwell, FEMS Microbiology Immunology, 47:341-350 (1989).
Brown et al., Inflammatory Bowel Diseases, 10:546-556 (2004).
Caplan et al., "Bifidobacterial supplementation reduces the incidence of necrotizing enterocolitis in a neonatal rat model", Gastroenterology, Sep. 1, 1999, pp. 577-583, vol. 117, No. 3.
Chen et al., Probiotics and prebiotics: role in clinical disease states. Adv Pediatr. 2005;52:77-113.
Cooper et al., Gastroenterology, 95:686-693 (1988).
Cordon-Cardo C., et al, "Immunohistologic expression of blood-group antigens in normal human gastrointestinal tract and colonic carcinoma", International Journal of Cancer, May 15, 1986, pp. 667-676, vol. 37, No. 5, Alan R. Liss, Inc.
D'Adamo et al., Alternative Medicine Review, 6:390-410 (2001).
Gokman-Polar et al., Cancer Research, 61:1375-1381 (2001).
Hallstrom et al., Eur. J. Clin. Microbiol. Infect. Dis., 23:463-470 (2004).
Haynes et al., Electrophoresis, 19:1862-1871 (1998).
Heneghan et al., FEMS Immunology and Medical Microbiology, 20:257-266 (1998).
Ikehara et al., Cancer Epidemiology, Biomarkers & Prevention, 10:971-977 (2001).
Kafetzis et al., "Neonatal necrotizing enterocolitis: an overview", Current Opinion in Infectious Diseases, Aug. 2003, pp. 349-355, vol. 16, No. 4, Lippincott Williams & Wilkins.
Kim et al., Cancer Research, 46:5985-5992 (1986).
Kobayashi et al., Amer. J. Gastroenterology, 88:919-924 (1993).
Konopka et al., PNAS 83:4049-4052 (1986).
Leiper et al., Gastroenterology, 120:A.525 (2001).
Lewin, Genes VI, 29:847-848 (1997).
Madjd et al., Breast Cancer Research, 7:R780-787 (2005).
Morrow et al., Human milk oligosaccharides are associated with protection against diarrhea in breast-fed infants. J Pediatr. 2003; 53(4): 167A.
Morrow et al., Human-milk glycans that inhibit pathogen binding protect breast-feeding infants against infectious diarrhea. J Nutr. May 2005;135(5):1304-7.
Newburg et al., Human milk glycans protect infants against enteric pathogens. Annu Rev Nutr. 2005;25:37-58.
Newburg et al., α1,2-linked fucosyloligosaccharides comprise a major component of the innate immune system of human milk. Glycobiology 2003; 13(11):8845.
Pendu, Histo-blood group antigen and human milk oligosaccharides: genetic polymorphism and risk of infectious diseases. Adv Exp Med Biol. 2004;554:135-43. Review.
Pennica et al., Proc. Nal. Acad. Sci, 95:14717-14722 (1998).
Saiman et al., Pediatric Infectious Disease Journal, 19(4):319-324 (2000).
Snelling, Current Opinion in Infectious Diseases, 18(5):420-426 (2005).
Thomsson et al., Glycobiology, 15(8):791-804 (2005).
Treszl et al., "Genetic basis for necrotizing enterocolitis—risk factors and their relations to genetic polymorphisms", Frontiers in Bioscience: A Journal and Virtual Library, Jan. 1, 2006, pp. 570-580, vol. 11.
Tsuboi et al., Annals of Surgical Oncology, 14:1880-1889 (2007).
Ziemer et al., An Overview of Probiotics, Prebiotics and Synbiotics in the Functional Food Concept: Perspectives and Future Strategies International Dairy Journal. 1998; 8:473-79.
Albermann, "Synthesis of the milk oligosaccharide 2'-fucosyllactose using recombinant bacterial enzymes," Carbohydrate Research 334 (2001): 97-103.
Bode et al., "Inhibition of monocyte, lymphocyte, and neutrophil adhesion to endothelial cells by human milk oligosaccharides," Thrombosis and Haemostasis, Schattauer GMBH, DE; US, vol. 92, No. 6, Dec. 1, 2004: 1402-1410.
Chaturvedi et al., Fucosylated human milk oligosaccharides vary between individuals and over the course of lactation. Glycobiology. May 2001;11(5):365-72.
Cregg et al., "Recombinant protein expression in *Pichia pastoris*", Mol. Biotechnol., 16: 23-52,2000.
Daddaoua et al., The Journal of Nutrition, 136(3):672-676 (2006).
Dai et al., "Role of oligosaccharides and glycoconjugates in intestinal host defense," J. Ped. Gastroenterol, vol. 30(2): S23-S33, 2000.
Dean et al., The VRG4 gene is required for GDP-mannose transport into the lumen of the Golgi in the yeast, *Saccharomyces cerevisiae*. J Biol Chem. Dec. 12, 1997;272(50):31908-14.
Franz-Georg Hanisch et al., "Structures of acidic O-linked polylactosaminoglycans on human skim milk mucins," Glycoconjugate Journal, Dec. 31, 1990: 525-543.
Franz-Georg Hanisch et al., "Structures of neutral o-linked polylactosaminoglycans on human skim milk mucins," The Journal of Biological Chemistry, Jan. 15, 1989: 872-883.
Gao et al., Identification of a conserved motif in the yeast golgi GDP-mannose transporter required for binding to nucleotide sugar. J Biol Chem. Feb. 9, 2001;276(6):4424-32. Epub Nov. 6, 2000.
Grazioso et al., Antiinflammatory effects of human milk on chemically induced colitis in rats. Pediatr Res. Nov. 1997;42(5):639-43.
Hurd et al., "Increased Susceptibility of Secretor Factor Gene *Fut2*-Null Mice to Experimental Vaginal Candidiasis," Infection and Immunity, Jul. 2004: 4279-4281.
Jiang, Z. et al., "Prevalence of enteric pathogens among international travelers . . . " J. Infect. Dis. (2002), vol. 185: 497-502.
Kunz et al., "Potential Anti-Inflammatory and Anti-Infectious Effects of Human Milk Oligosaccharides," Bioactive Components of Milk (Book Series: Advances in Experimental Medicine and Biology, Springer Science & Business Media, New York, NY, US, XP009136897, ISBN: 978-0-387-74086-7: 455-465. 2008.
Kunz, C. et al., "Oligosaccharides in human milk . . . " Ann. Rev. Nutr. (2000) vol. 20: 699-722.
Lara-Villoslada et al., Clinical Nutrition, 25(3):477-488 (2006).
Maki, "Conversion of GDP-Mannose into Various GDP-Deoxyhexoses in Gram-Negative Bacteria," University of Helsinki, Jun. 16, 2003: 1-63.
Mattila et al., "Functional expression of *Escherichia coli* enzymes synthesizing GDP-L-fucose from inherent GDP-D-mannose in *Saccharomyces cerevisiae*," Glycobiology, vol. 10, No. 10: 1041-1047, 2000.
Newburg et al., Human milk alpha1,2-linked fucosylated oligosaccharides decrease risk of diarrhea due to stable toxin of *E. coli* in breastfed infants. Adv Exp Med Biol. 2004;554:457-61.
Newburg, DS, "Human Milk Glycoconjugates that Inhibit Pathogens," Current Medicinal Chemistry, Bentham Science Publishers BV, BE, vol. 6, No. 2, Jan. 1, 1999: 117-127.
Podolsky, D. et al., "Development of anti-human colonic mucin monoclonal antibodies," J. Clin. Invest. (1986), vol. 77: 1251-1262.
Pradel, N., et al., "Prevalence and characterization of shiga toxin . . . " J. Clin. Microbiol. (2000), vol. 38, No. 3: 1023-1031.
Prestwich, G., et al., "Controlled chemical modification of hyaluronic acid . . . " J. Controlled Release (1998), vol. 53: 93-103.
Ruiz-Palacios et al., "*Campylobacter jejuni* Binds Intestinal H(O) Antigen (Fucα1, 2 Galβ1, 4GlcNAc), and Fucosyloligosaccharides of Human Milk Inhibit Its Binding and Infection," The Journal of Biological Chemistry, vol. 278, No. 16: 14112-14120, 2003.
Sharon, N. et al.,. "Safe as mother's milk . . . " Glycoconj. J. (2000), vol. 17: 659-664.

(56) References Cited

OTHER PUBLICATIONS

Spik et al., Primary and three-dimensional structure of lactotransferrin (lactoferrin) glycans. pp. 21-32 from Lactoferrin: Structure and Function, T.W. Hutchens, ed. Plenum Press, New York, 1994.

Spik, G. et al., "Primary structure of the glycans . . ." Eur. J. Biochem. (1982), vol. 121: 413-419.

Stromqvist, M. et al., "Human milk k-casein and inhibition of *Helicobacter pylori* . . ." J. Ped. Gastro. Nutr. (1995), vol. 21: 288-296.

Thurl et al., Quantification of individual oligosaccharide compounds from human milk using high-pH anion-exchange chromatography. Anal Biochem. Mar. 15, 1996;235(2):202-6.

Wakabayashi et al., Lactoferrin research, technology and applications. Int. Dairy J. 2006;16:1241-51.

Wilson, N. et al., "Glycoproteomics of milk . . ." J. Proteome Res. (2007), vol. 7: 3687-3696.

Wu et al., "Identification and characterization of GDP-D-mannose 4,6-Dehydratase . . ." Biochem Biophvs. Res. Comm., 285: 364-371, 2001.

Yolken, R. et al., "Human milk mucin inhibits rotovirus . . ." J. Clin. Invest. (1992), vol. 90: 1984-1991.

Buescher. Anti-inflammatory characteristics of human milk: how, where, why. Adv Exp Med Biol. 2001;501:207-22.

Chaturvedi et al., Milk oligosaccharide profiles by reversed-phase HPLC of their perbenzoylated derivatives. Anal Biochem. Aug. 15, 1997;251(1):89-97.

Frost et al., The importance of pro-inflammatory signaling in neonatal necrotizing enterocolitis. Semin Perinatol. Apr. 2008;32(2):100-6. doi: 10.1053/j.semperi.2008.01.001.

Moss et al., Th1/Th2 cells in inflammatory disease states: therapeutic implications. Expert Opin Biol Ther. Dec. 2004;4(12):1887-96.

Sisk et al., Early human milk feeding is associated with a lower risk of necrotizing enterocolitis in very low birth weight infants. J Perinatol. Jul. 2007;27(7):428-33. Epub Apr. 19, 2007. Erratum in: J Perinatol. Dec. 2007;27(12):808.

Urashima et al., Oligosaccharides of milk and colostrum in non-human mammals. Glycoconj J. May 2001;18(5):357-71.

Reinhard et al., Image analysis method to assess adhesion of *Helicobacter pylori* to gastric epithelium using confocal laser scanning microscopy. J Microbiol Methods. Feb. 2000;39(3):179-87.

Updegrove, Necrotizing enterocolitis: the evidence for use of human milk in prevention and treatment. J Hum Lact. Aug. 2004;20(3):335-9.

Lin et al., Oral probiotics reduce the incidence and severity of necrotizing enterocolitis in very low birth weight infants. Pediatrics. Jan. 2005; 115(1):1-4.

\* cited by examiner

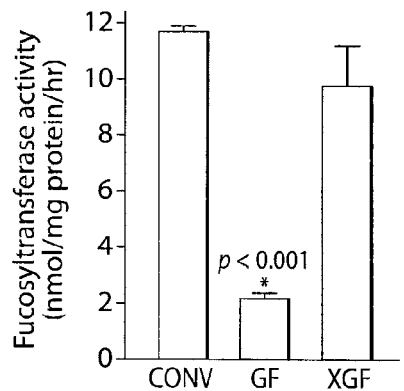
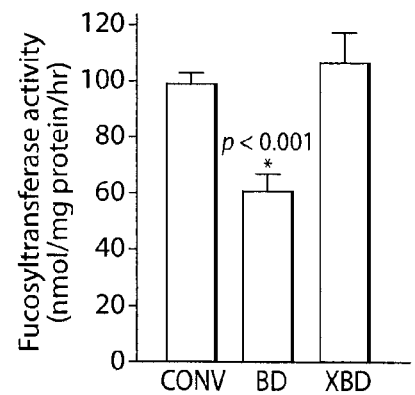
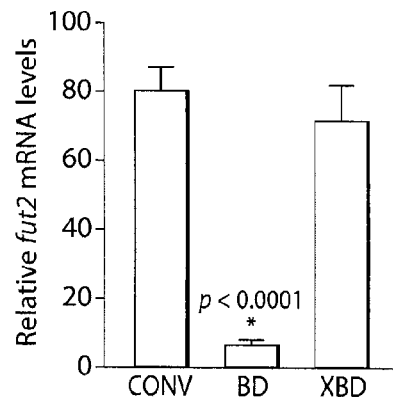
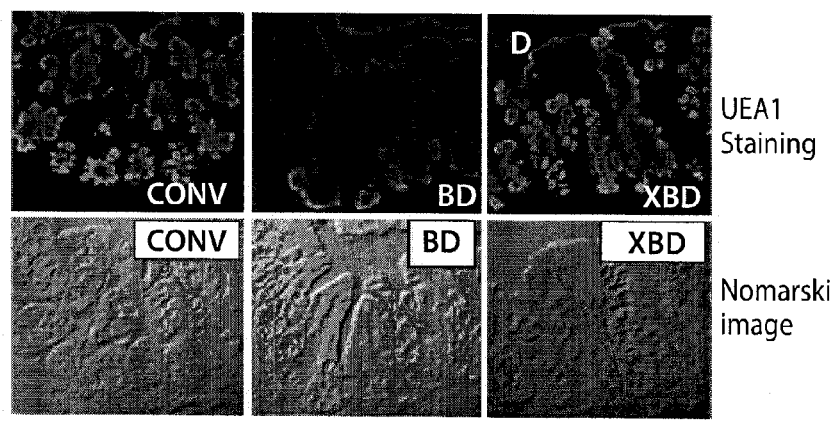
FIGURE 1D

CART Trees

Model A. Tree obtained from entry of all antigens as catergorical variables into the model

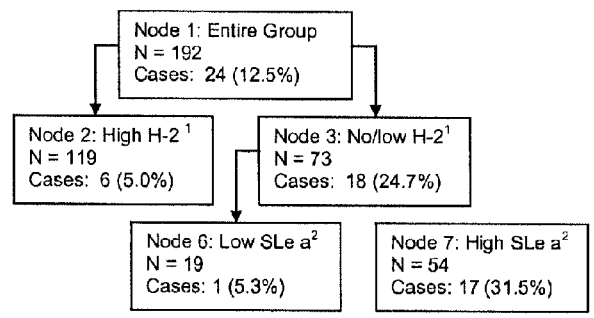

Model B. Tree obtained from entry of the 3 final nodes of Model A into a single model

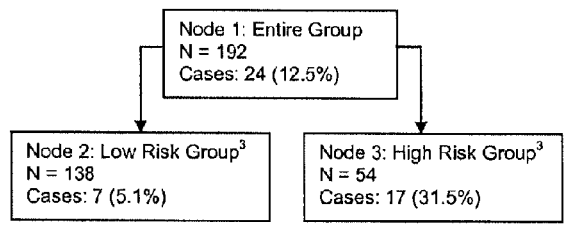

[1]Non-secretors and low H-2 secretors (salivary H-2 O.D. ≤ 0.627) form one node; the high secretors (salivary H-2 O.D. > 0.627) form the other node
[2]High SLe a salivary expression defined as O.D.> 0.318; low defined as O.D. ≤ .318
[3]High risk group: low to no H-2 (OD<0.627) and high risk SLe a (OD>.318)

FIGURE 5

```
   1 agtcaccgat gctggaaggg tttctttggc cctgagtgaa gagagaccca gagggaacac
  61 tgaggtgcct gcccaaccac tctgtcccgg tttccttcag caggaccagg tgagagaagc
 121 catgctggtc gttcagatgc ctttctcctt tccatggcc cacttcatcc tctttgtctt
 181 tacggtttcc actatatttc acgttcagca gcggctagcg aagattcaag ccatgtggga
 241 gttaccggtg cagataccag tgctagcctc aacatcaaag gcactgggac ccagccagct
 301 caggggatg tggacgatca atgcaatagg ccgcctgggg aaccagatgg gcgagtacgc
 361 cacactgtac gccctggcca agatgaacgg gcggcccgcc ttcatcccgg cccagatgca
 421 cagcaccctg gcccccatct tcagaatcac cctgccggtg ctgcacagcg ccacggccag
 481 caggatcccc tggcagaact accacctgaa cgactggatg gaggaggaat accgccacat
 541 cccgggggag tacgtccgct tcaccggcta ccctgctcc tggaccttct accaccacct
 601 ccgccaggag atcctccagg agttcaccct gcacgaccac gtgcgggagg aggcccagaa
 661 gttcctgcgg ggcctgcagg tgaacgggag ccggccgggc acctttgtag gggtccatgt
 721 tcgccgaggg gactatgtcc atgtcatgcc aaaagtgtgg aaggggtgg tggccgaccg
 781 gcgataccta cagcaggccc tggactggtt ccgagctcgc tacagctccc tcatcttcgt
 841 ggtcaccagt aatggcatgg cctggtgtcg ggagaacatt gacacctccc acggtgatgt
 901 ggtgtttgct ggcgatggca ttgagggctc acctgccaaa gatttgctc tactcacaca
 961 gtgtaaccac accatcatga ccattgggac gttcgggatc tgggccgcat acctcacggg
1021 cggagacacc atctacctgg ccaattacac cctccccgac tcccctttcc tcaaaatctt
1081 taagccagag gcagccttcc tgccggagtg gacagggatt gccgcagacc tgtcccccctt
1141 actcaagcac taatgctggc ccattctttg agaccttttc tccttctctg cctccctcaa
1201 gatgagtgcc cgggcatgag aagcacatgg ttccatgagc aggacccatc tctcttctgt
1261 gaagatgcgt tgggctgcaa gtaacagaaa tctcagtgaa cagtggcctg gcgtggtggc
1321 tcatgcctgt aatgctcgca ctttgtgagg ccagggtggg tggatcactt gaggtcagga
1381 gttcaagact agcctggcca acatggtgaa accccatctc gactaaaaat acaaaaatta
1441 gccaggcgtg gtggtgcaca cctgtaatcc cagctactcg ggaggctgag gcaagagaat
1501 cacttgaacc caggaggcgg aggttgcagt gagccaagat ggtgccgctg cactccagtc
1561 tgggtgacac agcaagactc catctcaaaa aaaaaaaaa aaaaagaaa agaaaaagaa
1621 atgaatgggt tcaaagacca taatcatgca tatcacataa gaccagaagt ggcccaggtc
1681 cagggtcagt taatttagcg gctccacaaa gtcatcagtc acctgagctc catccatctt
1741 cacatgctgt gctaccattt cttagctgta tcatcccatg gtcccaaaag ggctgctaca
1801 catccagcca tcacatgcag ataattcctt tcaaaaacag cagaaagagg ctcgttcttg
1861 tcttggtccc ttttgaagaa tgaatgaaac cttcctaagc cttccagcaa tttccccccca
1921 actccgatgg gtaggaattg tcacataccc atgtgaccg ataggaggca aaagaaatga
1981 gacttctgag attagtttag cctcagattc tgcagctgag aagttgatca gccacctctg
2041 aaggacatgc agcttgcaga aaattagggt ggtgttacca aggtgaaaag gggaaatggc
2101 tttagagtag acaacagaga tgccctgagg ggttgtgtag gttgttcact gcaggaagtc
2161 ccctggttaa gaaggcaagt ggggtttaaa cagacccaca gtctactcat caaaccaggt
2221 gtccttggca ttgtgtccac ccagagagct cactgttttc ttttcttttt cttttcttttt
2281 ttttttttt tttgagatgg agtcttgctg catccccag gctggagtgc agtggcatga
2341 tcttggctca ctgcagcctc cgcctccag gttcaagcga ttctcctgcc tcagcctccc
2401 gagtagctag gattacaggt gcgtgccacc acgcccagct aatttttata tgtttagtgg
2461 aaatggagtt tcaccatgtt ggtcaggctg gtctcaaact cctgacctca tgatccgcct
2521 tcctcggcct cccaaagtgc tgggattaca ggtgttagcc actgcgcccg gcccctagagc
2581 tcactgtttt ctagttagtc catctggaag tggagccttt ttccagtttg cacaaatgtg
2641 ccatattggc ttgtagctgg catgcatcca agtccatagg tcctgcctct tcaatcctgg
2701 ctttctaggg cctgggatga tcattgctag aactgagaga ccagcctggc tcagtgaact
2761 tcagggcgtt ccgttcattc tttcagtaaa tgtttgcagc acatgtgtta catgtcaggc
2821 agtgaaaccc cccacagcag ccttccctct cagaggatac atttgtaacc attacacagt
2881 catcaaagga ataatttttt ttaatcacca gtgtgcatac agtcatggag ttgggtattc
2941 ccagctacca gggaggctga ggtgggagga ttgcttgatg ccaggagtta gggaatatag
3001 tgcaccgtga ttggacttgc gaatagccac tgcactgcgg cctgacgac gtagtgatac
3061 cctgactctt ataaataaat aaatgaataa acacaattat gactttgcgg atggg
```

FIGURE 7

```
  1 mlvvqmpfsf pmahfilfvf tvstifhvqq rlakiqamwe lpvqipvlas tskalgpsql
 61 rgmwtinaig rlgnqmgeya tlyalakmng rpafipaqmh stlapifrit lpvlhsatas
121 ripwqnyhln dwmeeeyrhi pgeyvrftgy pcswtfyhhl rqeilqeftl hdhvreeaqk
181 flrglqvngs rpgtfvgvhv rrgdyvhvmp kvwkgvvadr rylqqaldwf rarysslifv
241 vtsngmawcr enidtshgdv vfagdgiegs pakdfalltq cnhtimtigt fgiwaayltg
301 gdtiylanyt lpdspflkif kpeaaflpew tgiaadlspl lkh
```

FIGURE 8

USE OF SECRETOR, LEWIS AND SIALYL ANTIGEN LEVELS IN CLINICAL SAMPLES AS PREDICTORS OF RISK FOR DISEASE

RELATED APPLICATION INFORMATION

This application is a divisional application of U.S. patent application Ser. No. 13/006,795, filed Jan. 14, 2011, which is a continuation application of U.S. patent application Ser. No. 12/205,089, filed Sep. 5, 2008, which claims the benefit of U.S. provisional application Ser. No. 60/970,902, filed Sep. 7, 2007. The contents of the prior applications are incorporated herein by their entireties.

GOVERNMENT SUPPORT

This invention was made with government support under HD013021 awarded by the National Institutes of Health. The government has certain rights in this invention.

TECHNICAL FIELD

This disclosure relates to the field of medical diagnostics and more particularly to materials and methods for assessing and treating inflammatory and infectious disorders in infancy.

BACKGROUND

Inflammatory and infectious disorders in infancy can be associated with serious morbidity and mortality. Inflammatory and infectious disorders that occur perinatally, for example, necrotizing enterocolitis (NEC), sepsis, and chorioamnionitis are major contributors to neonatal mortality rates. NEC, the most common gastrointestinal medical and/or surgical emergency occurring in neonates, occurs in 7-13% of very low birthweight infants, and is characterized by bowel injury and intestinal necrosis. NEC mortality rates overall are in the range of 20-40%, and mortality rates for premature infants have been reported to exceed 50%. Surgical intervention is required in about 30% of cases, and surgery-associated mortality is reported to be as high as 50%.

Survivors of inflammatory and infectious disorders of infancy can have significant short-term and long-term morbidities, including metabolic complications, recurrent infections, poor neurodevelopmental outcomes, and poor growth outcomes, that in some instances may require repeated surgical intervention and prolonged hospitalization.

SUMMARY

The methods described herein are based, in part, on our discovery of methods for assessing whether an infant is at high risk of death, or likely to develop certain inflammatory or infectious disorders, for example, necrotizing enterocolitis, sepsis, gastrointestinal infections, respiratory infections, and urinary tract infections. Disclosed herein is a method of identifying an individual at risk for necrotizing enterocolitis, the method comprising:

(a) measuring the level of at least one secretor antigen in a biological sample from the individual, and (b) comparing the measured level of the at least one secretor antigen to a predetermined value or a predetermined range of values, wherein the individual is at risk for necrotizing enterocolitis if the measured level of the at least one secretor antigen differs from the predetermined value or is outside the predetermined range of values.

In various embodiments: the individual is an infant (e.g., infant is a neonate, a low birthweight infant, an extremely low birthweight infant or a premature infant); the at least one secretor antigen comprises an α1,2-linked fucose antigen and/or an α2,3 sialylated antigen; the at least one secretor antigen is selected from the group consisting of: the H-1, H-2, Lewis$^b$ and Lewis$^y$ antigens and derivatives thereof; the derivative is a sialylated form of Lewis a, Lewis x, Lewis b or Lewis y; the derivative is a sulfated form of H-1, H-2, Lewis a, Lewis x, Lewis b or Lewis y; the biological sample is a bodily fluid or a tissue; the bodily fluid comprises saliva, blood, plasma, serum, urine, stool, amniotic fluid, hmucus, tears or lymph; the bodily fluid comprises saliva; the measuring step comprises an immunoassay; the at least one secretor antigen is selected from the group consisting of: H-1, H-2, Lewis$^b$ and Lewis$^y$ and derivatives thereof and wherein the individual is determined to be risk for necrotizing enterocolitis if the measured level is below the predetermined value or below the predetermined range of values; the predetermined value or the predetermined range of values represents the average level of the at least one secretor antigen in a population of individuals determined to be secretors; the individual is determined to be at risk for necrotizing enterocolitis when the measured level of at least one secretor antigen is at least 10% less than the average level found in a control population of secretors; the at least one secretor antigen is the H-2 antigen.

In some cases the at least one antigen is sialyl Lewis a or derivative thereof and the individual is determined to be risk for necrotizing enterocolitis if the measured level is above the predetermined value or above the predetermined range of values. In some embodiments of this method: the infant is a neonate, a low birthweight infant, an extremely low birthweight infant or a premature infant, the biological sample is a bodily fluid or a tissue; the bodily fluid comprises saliva, blood, plasma, serum, urine, stool, amniotic fluid, mucus, tears or lymph; the bodily fluid comprises saliva; the measuring step comprises an immunoassay; and the predetermined value or the predetermined range of values represents the average level of the at least one secretor antigen in a population of individuals determined to be secretors.

Also disclosed is a method of identifying an individual at risk for developing a gastrointestinal disorder, the method comprising:

(a) measuring the level of at least one secretor antigen in a biological sample from the individual, and (b) comparing the measured level of the at least one secretor antigen to a predetermined value or a predetermined range of values, wherein the individual is at risk for a developing a gastrointestinal disorder if the measured level of the at least one secretor antigen differs from the predetermined value or is outside the predetermined range of values.

In various embodiments of this method: the individual is an infant (e.g., a neonate, a low birthweight infant, an extremely low birthweight infant or a premature infant); the measured antigens comprise an α1,2-linked fucose antigen and/or an α2,3 sialylated antigen; the secretor antigen is selected from the group consisting of: the H-1, H-2, Lewis$^b$ and Lewis$^y$ antigens and derivatives thereof; the derivative is a sialylated form of Lewis a, Lewis x, Lewis b or Lewis y; the derivative is a sulfated form of Lewis a, Lewis x, Lewis b or Lewis y; the biological sample is a bodily fluid or a tissue; the bodily fluid comprises saliva, blood, plasma, serum, urine, stool, amniotic fluid, mucus, tears or lymph; the measuring step comprises an immunoassay; the at least one secretor antigen is selected from the group consisting of: H-1, H-2, Lewis$^b$ and Lewis$^y$ and derivatives thereof and wherein the individual is determined to be risk for developing a gastrointestinal disorder if the measured level is below the predetermined value or below the predetermined range of values; the predetermined value or the predetermined range of values represents the average level of the at least one secretor antigen in a population of individuals determined to be secretors; the individual is determined to be at risk for necrotizing enterocolitis when the measured level of the at least one secretor antigen is at least 10% less than average level found in control population of secretors; the at least one antigen is the H-2 antigen; the gastrointestinal disorder is gastrointestinal inflammation; the gastrointestinal disorder is gastrointestinal infection; the disorder is late onset sepsis; an the gastrointestinal infection comprises infection with one or more of *Staphylococcus* spp., *Staphylococcus aureus*, *Escherichia coli*, *Streptococcus* spp., *Enterobacter* spp., *Klebsiella* spp., *Bacillus* spp., *Serratia* spp., *Candida* spp, Norwalk and other Noroviruses, *Campylobacter* spp, *Vibrio cholerae*, *Bacteriodes* spp., Clostridiae, Giardia.

Also disclosed is a method comprising:

(a) measuring the level of at least one secretor antigen in a biological sample from the individual, and (b) comparing the measured level of the at least one secretor antigen to a predetermined value or a predetermined range of values, (c) determining that the individual is at risk for necrotizing enterocolitis if the measured level of the at least one secretor antigen differs from the predetermined value or is outside the predetermined range of values; and (d) taking steps to treat or reduce the risk for necrotizing enterocolitis if the individual is determined to be at risk for necrotizing enterocolitis.

In this method (d) can comprise administering to the individual one or more of α1,2 fucosyl glycans, probiotic organisms or prebiotics.

Also disclosed is a method of identifying an individual at risk for necrotizing enterocolitis, the method comprising:

(a) measuring the level of FUT2 protein or mRNA encoding FUT2 in a biological sample from the patient;

(b) comparing the measured level of level of FUT2 protein or mRNA encoding FUT2 to a predetermined value or a predetermined range of values, wherein the individual is at risk for necrotizing enterocolitis if the measured level of FUT2 protein or mRNA encoding FUT2 is below a predetermined value or a predetermined range of values.

Disclosed herein is a method of identifying an individual at risk for necrotizing enterocolitis, the method comprising:

(a) providing a biological sample from the individual;

(b) determining whether the individual harbors a FUT2 gene having genetic change that reduces the expression or activity of FUT2, wherein the individual is at risk for necrotizing enterocolitis if the individual harbors a FUT2 gene having genetic change that reduces the expression or activity of FUT2.

Disclosed herein is a method of identifying an individual (e.g., an infant) at risk for death, the method comprising:

(a) measuring the level of at least one secretor antigen in a biological sample from the individual, and (b) comparing the measured level of the at least one secretor antigen to a predetermined value or a predetermined range of values, wherein the individual is at risk for necrotizing enterocolitis if the measured level of the at least one secretor antigen differs from the predetermined value or is outside the predetermined range of values.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1: Fucosyltransferase and Fut2 mRNA expression in mouse colon. (A) α1,2/3-fucosyltransferase in conventional [CONV], germ-free (GF) and ex-germ-free (XGF) mice; (B) α1,2/3-fucosyltransferase activity and (C) Fut2 mRNA in the CONV, bacteria-depleted (BD) and bacteria-repleted (XBD) mice; (D) α1,2-fucosylated glycan expression detected by UEA-1 lectin and corresponding Nomarski image.

FIG. 5: Schematic depiction of CART analysis.

FIG. 7: Sequence of human "secretor" FUT2 mRNA.

FIG. 8: Sequence of human "secretor" FUT2 polypeptide.

DETAILED DESCRIPTION

Figure 2B:
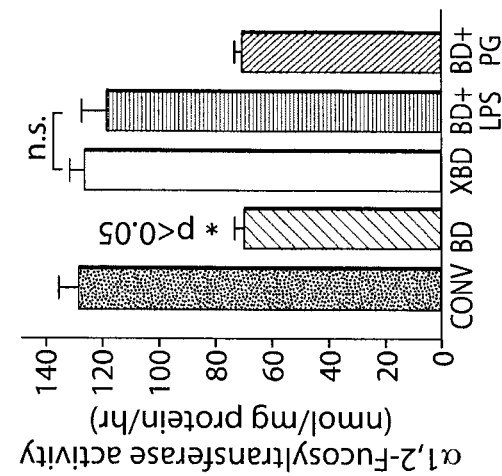
FIG. 2: (A) TLR4 expression is necessary for bacterial activation of intestinal fucosylation. (B) TLR4 ligands are sufficient for activation of mucosal fucosylation in bacteria-depleted mice.

The ABH and Lewis histo-blood group antigens are carbohydrates representing the terminal structures of glycan chains. The H-type histo-blood group antigens, for example, the H type 1 and 2, the Lewis$^b$ and the Lewis$^y$ antigens, are characterized by a fucose terminus in an α1,2 linkage. In mammals, the H-type histo-blood group antigens are found on a wide range of tissue types including epithelial cells of organs that are in direct contact with the external environment, e.g., the upper respiratory tract, the nasal epithelium and trachea, as well as the genito-urinary tract, ureter and vagina, as well as on erythrocytes, some neurons of the peripheral nervous system, thymus epithelium and the skin. In several human populations, about 80% of individuals also express H-type histo-blood group antigens in a soluble form in biological fluids, for example, saliva, breast milk, serum, tears, sweat and semen. In about the remaining 20% of individuals in these human populations, the soluble H-type histo-blood group antigens are either absent from, or found at extremely low levels, in biological fluids. These two phenotypes have been designated as "secretors" and "non-secretors" respectively and the soluble H-type histo-blood group antigens are typically referred to as secretor antigens. In other human populations the percentage of individuals who are non-secretors is lower than 20%.

The basis for the phenotypic difference between the secretor and non-secretor subpopulations stems from genetic polymorphisms in the FUT2 gene encoding the enzyme fucosyl transferase 2 also referred to in the art as alpha(1,2)fucosyltransferase 2, EC 2.4.1.69, SE 2, SEC2, Fucosyltransferase-2 (secretor), GDP-L-fucose:beta-D-galactoside 2-alpha-L-fucosyltransferase 2, Galactoside 2-alpha-L-fucosyltransferase 2, Secretor blood group alpha-2-fucosyltransferase, Secretor factor, and transmembrane protein 2. The FUT2 gene is also referred to in the art as the secretor gene (Se).

The FUT2 gene product, FUT2, catalyzes the formation of an α-L-fucosyl-1,2-β-D-galactosyl-R structure from GDP-β-L-fucose and β-D-galactosyl-R, where R can be a glycoprotein or a glycolipid. FUT2 is expressed in many organs that generally are of endodermal origin including gut, pharynx, liver, respiratory tract, bladder, urethra and endocrine glands, although within those organs FUT2 expression is also a function of the differentiation pattern of the tissue, e.g., keratinized vs. non-keratinized squamous epithelium, ducts vs. acini of glandular tissues, as well as the particular cell type, e.g, secretory vs. ciliated cells in the endometrium, and mucous vs. serous cells in the salivary gland. Secretors express functional FUT2; non-secretors fail to express functional FUT2. Accordingly, soluble H-type histo-blood group antigens are not synthesized and therefore not secreted into biological fluids of non-secretors.

The experiments described in the Examples indicate that the secretor status and the expression of sialyl glycan epitopes of an infant are correlated with risk of NEC and death. More specifically, extremely low birthweight infants (ELBW) or premature infants who expressed little or no H-2 antigens in saliva, as well as infants who expressed elevated levels of sialyl Lewis a antigens in saliva, are significantly more likely to experience adverse clinical outcomes such as NEC, late onset sepsis and death compared to infants who express moderate or high levels of H-2 antigen or infants who express little or no sialyl Lewis a antigens in saliva.

Disclosed herein are materials and methods relating to the identification of individuals as risk of developing an inflammatory or infectious disorder, for example, NEC, gastrointestinal infections, or late onset sepsis. More specifically, an infant can be identified as being at risk for an inflammatory or infectious disorder, for example, NEC, gastrointestinal infection or late onset sepsis, by assessing the secretor status of the infant. In some embodiments, an infant who does not express or who expresses low levels of secretor antigens relative to a reference sample can be classified as being at risk for NEC, gastrointestinal infection or late onset sepsis. In other embodiments, an infant who expresses elevated levels of sialyl Lewis a (sLe$^a$) antigen relative to a reference sample can be classified as being at risk for NEC, gastrointestinal infection or late onset sepsis.

Also provided herein are methods of treatment and management of individuals at risk of developing an inflammatory or infectious disorder, for example, NEC, gastrointestinal infections, or late onset sepsis. In some embodiments, an individual identified by secretor status as being at risk of developing NEC, gastrointestinal infection or late onset sepsis can be treated with specific therapies that include protective agents, e.g., probiotic organisms or prebiotic agents, including α1,2 fucosyl glycans. In some embodiments, the course of treatment of an individual identified by secretor status as being at risk of developing NEC, gastrointestinal infection or late onset sepsis can be evaluated by assessing the level of secretor antigens in the mother's milk being provided to her infant and, based on the levels of secretor antigens in the food source relative to a reference sample, administering to the infant specific therapies that include protective agents, e.g., α1,2 fucosyl glycans, probiotic organisms or prebiotics.

Secretor Antigens

Secretor antigens, i.e., the H type 1 and 2, the Lewis$^b$ and the Lewis$^y$ antigens, are glycans that include a fucose terminus in an α1,2 linkage. The term glycans as used herein refers to a compound of two or more subunit monosaccharide units joined together by a glycosidic bond, i.e., a covalent bond between an anomeric hydroxyl group, in α or β configuration, of one monosaccharide and any available hydroxyl group in a second monosaccharide, regardless of additional modifications e.g., linkages to other additional monosaccharide units, polypeptides, lipids or other biological or nonbiological molecules. We may refer to a saccharide polymer containing a small number, typically three to 35 or more component sugars as an oligosaccharide. All oligosaccharides described herein are described with the name or abbreviation for the non-reducing saccharide (i.e., Gal), followed by the configuration of the glycosidic bond (α or β), the ring bond (1 or 2), and then the name or abbreviation of the next saccharide (i.e., GlcNAc) toward the reducing end of the molecule. For a review of standard glycobiology nomenclature see, *Essentials of Glycobiology*, Varki et al., eds., 1999, Cold Spring Harbor Laboratory Press.

The specific form of the secretor antigen can vary and depends, in part, upon the structure of the minimal disaccharide precursor, or core sequence, from which the particular antigen was assembled. The core sequence can be either the lacto type I structure, galactose (β1-3) N-acetylglucosamine-R, which we abbreviate here as {Gal (β1-3)GlcNAc}-R or the lacto type II structure galactose (β1-4) N-acetylglucosamine-R, which we abbreviate here as {Gal(β1-4)GlcNAc}-R. In the minimal, unconjugated core sequence, R can be H or other small molecule radicals. The disaccharide precursor can also be conjugated to longer glycans as oligosaccharides, or as the glycan moieties of glycolipids, peptides, proteins, mucins, or other macromolecules.

Thus, for example, the H-1 antigen is derived from the type I precursor by FUT2 (or FUT1) catalyzed addition of a fucose residue to the galactose moiety of the type I precursor in an α1,2 linkage to generate the structure {Fucose(α1-2) Galactose (β1-3) N-acetylglucosamine, which we abbreviate as {Fuc (α1-2) Gal (β1-3) GlcNAc}. The H-1 antigen is a structural precursor to another secretor antigen, Lewis$^b$. The Lewis$^b$ secretor antigen includes the H-1 structure plus a second fucose residue in a non-terminal α1,4 linkage to the GlcNAc moiety in the configuration {Fucose(α1-2) Galactose (β1-3) [Fucose(α1-4)]N-acetylglucosamine} which we abbreviate as {Fuc (α1-2) Gal (β1-3) [Fuc (α1-4)] GlcNAc}.

Correspondingly, the H-2 antigen is derived from the type II precursor by FUT2 (or FUT1) catalyzed addition of a fucose residue to the galactose moiety of the type II precursor in an α1,2 linkage to generate the structure {Fucose(α1-2) Galactose (β1-4) N-acetylglucosamine}, which we abbreviate as {Fuc (α1-2) Gal (β1-4) GlcNAc}. The H-2 antigen is a structural precursor to another secretor antigen, Lewis$^y$. The Lewis$^y$ secretor antigen includes the H-2 structure plus a second fucose residue in a non-terminal α1,3 linkage to the GlcNAc moiety in the configuration {Fucose(α1-2) Galactose (β1-4) [Fucose(α1-3)]N-acetylglucosamine} which we abbreviate as {Fuc (α1-2) Gal (β1-4) [Fuc (α1-3)] GlcNAc}.

A secretor antigen may comprise a single α1,2 fucose substituted core sequence, wherein R is H or other small radicals. Alternatively, a secretor antigen can comprise a repetitive series of substituted core sequences, wherein R is another core sequence. The single core sequence or a repetitive core sequence may be present within a larger sugar. Accordingly, a secretor antigen-containing oligosaccharide can be, for example, a trisaccharide, a tetrasaccharide, a pentasaccharide, and so on. A secretor antigen can also be covalently linked to another macromolecule, e.g., a polypeptide or a lipid. The single substituted core sequence can also be linked directly to a polypeptide or lipid, e.g., R can be a protein or a lipid or can be present in a polysaccharide that is bound to a polypeptide or lipid. Secretor antigens may be covalently linked to polypeptides via N-linked glycosylation, that is, through an asparagine residue, or via O-linked glycosylation, for example, through serine, threonine, hydroxylproline, tyrosine or other hydroxyl containing residue. Glycoproteins that include secretor antigens include, for example without limitation, mucins, bile-salt-stimulated lipase (BSSL), and lactadherin. Examples of secretor antigen-bearing lipids include, without limitation, H-1 glycolipid, H-2 glycolipid, Le$^x$ glycolipid, and Le$^y$ glycolipid.

Lewis Antigens

The Lewis antigens can be present as any glycan containing Lewis epitopes, that is, containing H-1, H-2, Le$^a$, Le$^b$, Le$^x$, and/or Le$^y$ epitopes, which are α1,3 or a1,4-linked fucosylated oligosaccharide moieties. This includes free oligosaccharides, glycolipids, glycoproteins, mucins, glycosaminoglycans, and glycopeptides. Individuals can express glycans that express the H-1, H-2, Le$^a$, Le$^b$, Le$^x$, and/or Le$^y$ epitopes.

Sialyl Antigens

The sialyl antigens can be present as any glycan containing sialylated antigens, including free oligosaccharides, glycolipids (e.g., gangliosides), glycoproteins, mucins, glycosaminoglycans, and glycopeptides. Individuals can express sialylated epitopes, including gangliosides and other glycans that express the sialyl Lewis a (sLe$^a$), sLe$^b$, sLe$^x$, and/or sLe$^y$ epitopes.

Assaying Secretor Antigens

The level of one or more secretor antigens can be measured in any biological fluid known in the art to comprise secretor antigens. Examples of biological fluids include, without limitation, saliva, serum, blood plasma, breast milk, amniotic fluid, sweat, urine, tears, mucus, lymph, and stool. Biological fluid samples can be collected from an individual using any standard method known in the art that results in the preservation of secretor antigen structure. Saliva samples may be collected using cotton swabs, wipes, suction, scraping, or by having the individual rinse the mouth and expectorate into a tube or collector. Blood samples can be obtained via venous puncture techniques. Serum samples can be prepared from whole blood using standard methods such as centrifuging blood samples that have been allowed to clot. Plasma samples can be obtained by centrifuging blood samples that were treated with an anti-coagulant such as heparin. Breast milk can be collected by manual or mechanical expression. Biological fluid samples can be assayed for secretor antigens immediately following collection. Alternatively, or in addition, a biological fluid sample can be stored for later analysis using methods known in the art that preserve secretor antigen structure, e.g., freezing, drying, or freeze drying.

After determining the levels of specific secretor antigens in a biological sample, these levels can be compared with those of standard reference levels. Standard reference levels typically represent the average secretor antigen levels derived from a large population of individuals. The reference population may include individuals of similar age, body size, ethnic background or general health as the individual in question. The FUT2 genotype of the reference population may or may not be known. Thus, the secretor antigen levels in a patient's sample can be compared to values derived from: 1) individuals who express wild-type FUT2 and whose bodily fluids contain secretor antigens; 2) individuals who express variant forms of FUT2 and have moderate to low FUT2 activity and whose bodily fluids contain low levels of secretor antigens; or 3) individuals who have little or no FUT2 activity and whose bodily fluids lack secretor antigens.

In general, an elevated level of secretor antigen can be any level of a secretor antigen that is greater than either the level of a secretor antigen found in a control sample or greater than the average level of a secretor antigen found in samples from a population of normal healthy individuals who are secretors. A reduced level of a secretor antigen can be any level of a secretor antigen that is less than either the level of a secretor antigen found in a control sample or less than the average level of a secretor antigen found in samples from a population of normal healthy individuals who are secretors. Any population size can be used to determine the average level of a secretor antigen found in samples from a population of normal healthy individuals that are secretors. For example, a population of between 2 and 250, e.g., 2, 3, 4, 5, 10, 15, 20, 25, 30, 40, 50, 100, 150, 200, 250 or more individuals can be used to determine the average level of a secretor antigen in samples from a population of normal healthy individuals, with greater accuracy in the measurement coming from larger sample populations.

A reduced level of a secretor antigen can be 10, 20, 30, 50, 60, 70, 80, 90, 100, percent lower than that level found in a control sample or lower than the average level of a secretor antigen found in samples from a population of normal healthy individuals. In some cases, a reduced level of a secretor antigen can be 2, 3, 4, 5, 10, 20, 50 or more fold lower than that level found in a control sample or the average level of a secretor antigen found in samples from a population of normal healthy individuals.

In some cases, a reference chart can be used to determine whether or not a particular level of a specific secretor antigen in a sample is low or normal relative to a control sample or a larger population. For example, a reference chart can contain the normal range of secretor antigen levels found in healthy infants of the same age, gestational age, ethnic background or general health as the individual in question. Using this reference chart, any level of a secretor antigen measured in a sample can be classified as being low, normal, or elevated relative to a control sample or relative to an average value derived from a larger population.

Alternatively, or in addition, the level of a secretor antigen in a biological sample can be "normalized" against the level of one or more additional biological markers, for example another histo-blood group antigen, such as a P or sialyl antigen, whose expression is independent of the secretor status of the individual. That is, the levels of the additional marker can be evaluated in parallel with those of the secretor antigen, either at the same time or on a separate occasion. The additional marker can serve as an internal control for sample preparation, handling and storage as well as day-to-day assay variability. The values for the level of a secretor antigen and the additional marker may be expressed as a ratio and the ratio may be compared to similar ratio obtained for a reference sample or population. Examples of useful second markers include, but are not limited to, Lewis antigens whose expression is independent of the secretor (FUT2) expression, i.e., Lewis a and Lewis x. A Lewis antigen generally includes carbohydrates having as a core sequence either the lacto type I structure or the lacto type II structure substituted with one or more fucosyl residues. Thus, for example, a useful second marker can be Lewis a {Galactose ($\beta$1-3)[Fucose ($\alpha$1-4)]N-acetylglucosamine}, which we abbreviate as {Gal ($\beta$1-3) Fuc ($\alpha$1-4) GlcNac}, or Lewisx{Galactose ($\beta$1-4)[Fucose ($\alpha$1-3)]N-acetylglucosamine, which we abbreviate as {Gal ($\beta$1-4) [Fuc ($\alpha$1-3)] GlcNAc}, or the sialylated, sulfated, or sulfo-sialylated forms of these epitopes. Other commonly expressed non-Lewis blood group antigens could also be used, such as Lua (Lutheran a), P1 & P2 (the major antigens of the P blood group system), M&N, Fya &Fy b (antigens of the Duffy system), etc.

In addition, since stochastic variations in individual gene expression levels are common in biological systems, it may be desirable to normalize the level of a secretor antigen against a panel of two or more additional biological markers whose expression is known to be independent of the secretor status of the individual. This strategy may lead to greater accuracy in determining secretor antigen levels.

Once the relative level of a secretor antigen in an individual relative to that of a reference sample has been calculated, the individual's relative risk for gastroenteritis, necrotizing enterocolitis, late onset sepsis or death can be assessed. Any statistical method known in the art for evaluating relative risk may be used. One suitable method is Classification and Regression Tree (CART) characteristic curve analysis. CART analysis belongs to a family of nonparametric regression methods and is based on recursive partitioning to build a decision tree that optimizes the classification of individuals into high and low-risk groups. It can be applied to systematically identify cutpoints in continuous variables that maximize predictive value and minimize misclassification of cases and non-cases based on a balance between the sensitivity (i.e., the number of true cases detected) and the specificity (i.e., the accuracy) of a test. These two variables may also be considered positive predictive value and negative predictive value, and are correlated with diagnostic accuracy. The decision tree produced by CART analysis can be validated through Receiver Operating Curve (ROC) analysis to determine the area under the curve (AUC), which indicates the effectiveness of the relationship of the decision tree to discriminate between cases and non-cases.

In one example, CART analysis indicates that an individual classified as a low or non secretor, i.e, in the 38th percentile or below of H-2 salivary expression (as measured by O.D. values), has an increased risk for NEC and death. Thus, an individual whose levels of secretor antigens are in the 38th, 33rd, 30th, 25th, 20th, 15th, 10th, 5th, or lower percentile is 4 to 5 times more likely to suffer from NEC or death than individuals whose secretor antigen levels are above the 38th percentile. Among those who express little or no secretor antigen, the highest risk group is defined by those who also express high sialyl Lewis a antigen. Infants who express little or no secretor antigen and high sialyl Lewis a antigen have more than 6-fold the risk of NEC or death relative to all other infants. Thus, the high risk group can be defined either by little or no H-2 antigen alone or by the combination of little or no H-2 and moderate to high sialyl Lewis a antigen. Based on this comparison, as well as on other clinical indices, a clinician can predict the likelihood that a patient is at risk for NEC, and adjust treatment regimens accordingly.

The secretor status of an individual can be determined in a variety of ways. The level of a secretor antigen can be measured directly in a biological fluid. For example, the level of a secretor antigen can be measured using immuno-based assays, e.g., ELISA assays, radioimmunoassays, one or two dimensional gel electrophoresis coupled with immunodetection, or by using surface plasmon resonance-based biosensors, or by using chromatographic techniques, e.g., high performance liquid chromatography (HPLC) or gas chromatography (GC), or by spectrometry, e.g., mass spectrometry. Alternatively, or in addition, FUT2 activity can be measured in a biological sample using standard enzymology methods. In addition, FUT2 mRNA levels may be quantified (as a surrogate for levels of FUT2 activity in a biological sample) using a variety of methods well known to the art, e.g. RT-PCR or quantitative RT-PCR (for example: Kroupis C, Stathopoulou A, Zygalaki E, Ferekidou L, Talieri M, Lianidou E S. Clin Biochem. 2005 January; 38(1):50-7, Dyer J, Chisenhall D M, Mores C N. J Virol Methods. 2007 October; 145(1):9-13), or quantitative hybridization-based techniques such as cDNA or oligonucleotide microarrays (for example: Duggan D. J., Bittner M., Chen Y., Meltzer P. and Trent J. M. Nat Genet. 21(1 Suppl):$10^{-4}$ (1999); Cheung V. G., Morley M., Aguilar F., Massimi A., Kucherlapati R. and Childs G. Nat Genet. 21(1 Suppl):15-9 (1999)).

The human secretor FUT2 mRNA sequence is shown in FIG. 7 (GenBank® Accession No NM_000511.4) and the human secretor FUT2 protein sequence in shown in FIG. 8 (GenBank® Accession No. NP 000502.4).

Finally, the FUT2 genotype of an individual can be determined by single nucleotide polymorphism analysis (SNP) or RT-PCR-based techniques.

Immunoassays

Immunoassay methods are well known to those in the art. Antibody reagents that detect specific secretor Lewis antigens, e.g., H-1, H-2, Lewis$^b$, and Lewis$^y$, and other Lewis antigens. e.g., Lewis$^a$ and Lewis$^x$, can be generated using standard methods for antibody production or purchased from commercial sources. Antibodies can be monoclonal or polyclonal or any combination thereof. Useful antibodies can include: monoclonal and polyclonal antibodies, single chain antibodies, chimeric antibodies, bifunctional/bispecific antibodies, humanized antibodies, human antibodies, and complementary determining region (CDR)-grafted antibodies, that are specific for the secretor or glycan epitope, and also include antibody fragments, including Fab, Fab', F(ab')2, scFv, Fv, camelbodies, or microantibodies. In addition nucleic acid or peptide aptamer reagents capable of specifically binding to and detecting specific secretor antigens can be generated using standard published methods (e.g. The use of aptamers in large arrays for molecular diagnostics, Brody E. N., Willis M. C., Smith J. D., Jayasena S., Zichi D. and Gold L. *Mol Diagn* 4(4):381-8 (1999)).

Thus, in some embodiments, a specific anti-H-1, anti-H-2, anti-Lewis$^b$, or anti-Lewis$^y$ monoclonal antibody or aptamer can have a binding affinity less than about $1 \times 10^5$ Ka for an antigen other than H-1 and H-2, Lewis$^b$, and Lewis$^y$, respectively. In some embodiments, the anti-H-1, anti-H-2, anti-Lewis$^b$, or anti-Lewis$^y$ antibody is a monoclonal antibody that binds to H-1, H-2, Lewis$^b$, and Lewis$^y$ with an affinity of at least $1 \times 10^8$ Ka.

Any form of H-1 and H-2, Lewis$^b$, and Lewis$^y$ can be used to generate the anti-H-1 anti-H-2, anti-Lewis$^b$, and anti-Lewis$^y$ antibodies or aptamers respectively, including, minimal trisaccharide or disaccharide structures or epitope-bearing fragments thereof, and any glycan containing these epitopes. Highly suitable anti-H-1 anti-H-2, anti-Lewis$^b$, and anti-Lewis$^y$ antibodies or aptamers are those of sufficient affinity and specificity to recognize and bind to their respective targets in vivo. As used herein, the term epitope refers to an antigenic determinant of a glycan.

Specific carbohydrate binding antibodies or aptamers can be molecules that 1) exhibit a threshold level of binding activity; and/or 2) do not significantly cross-react with known related glycan molecules. The binding affinity of an antibody or aptamer can be readily determined by one of ordinary skill in the art, for example, by Scatchard analysis (Scatchard, Ann. NY Acad. Sci. 51: 660-672, 1949). In some embodiments the antibodies or aptamers can bind to their target epitopes or mimetic decoys with at least 1.5-fold, 2-fold, 5-fold 10-fold, 100-fold, $10^3$-fold, $10^4$-fold, $10^5$-fold, $10^6$-fold or greater affinity for the target glycan than to other glycans having some homology to the target glycan.

In some embodiments the antibodies or aptamers bind with high affinity to H-1 or H-2, Lewis$^b$, or Lewis$^y$ of $10^4$M or less, $10^{-7}$M or less, $10^{-9}$M or less or with subnanomolar affinity (0.9, 0.8, 0.7, 0.6, 0.5, 0.4, 0.3, 0.2, 0.1 nM or even less). In some embodiments the binding affinity of the antibodies or aptamers for H-1 or H-2, Lewis$^b$, or Lewis$^y$ is at least $1 \times 10^6$ Ka. In some embodiments the binding affinity of the antibodies or aptamers for H-1 or H-2, Lewis$^b$, or Lewis$^y$ is at least $5 \times 10^6$ Ka, at least $1 \times 10^7$ Ka, at least $2 \times 10^7$ Ka, at least $1 \times 10^8$ Ka, or greater. Antibodies or aptamers may also be described or specified in terms of their binding affinity to H-1 and/or H-2, Lewis$^a$, Lewis$^b$, Lewis', and/or Lewis$^y$. In some embodiments binding affinities include those with a $K_d$ less than $5 \times 10^{-2}$ M, $5 \times 10^{-5}$ M to $5 \times 10^{-7}$ M, $5 \times 10^{-8}$ M to $5 \times 10^{-10}$ M, $5 \times 10^{-12}$ M to $5 \times 10^{-14}$ M, or less.

Antibodies or aptamers can be purified by chromatographic methods known to those of skill in the art, including ion exchange and gel filtration chromatography (for example, Caine et al., Protein Expr. Purif. (1996) 8(2):159-166). Alternatively or in addition, antibodies or aptamers can be purchased from commercial sources, for example, Abcam, Biovendor Laboratory, Calbiochem, Signet Laboratories, Accurate Chemical and Scientific Corporation, and EMD.

Levels of secretor antigens can be measured in a biological sample using any immunoassay format known to those of skill in the art. For example, in non-competitive immunoassays, the secretor antigen is "sandwiched" between two antibodies, a capture antibody and a detection antibody. Typically, the capture antibody is bound either covalently or non-covalently to a solid phase, such as a tube or well, and the detection antibody is conjugated to an enzyme in the case of ELISA assays, or is radiolabeled in the case of RIA assays. In ELISA assays, the detection antibody can be covalently linked to an enzyme, or can itself be detected by a secondary antibody that is linked to an enzyme through bioconjugation. Specific antibody binding is analyzed by adding an enzymatic substrate, e.g., a chromogenic or fluorogenic molecule, which produces a detectable quantifiable signal upon cleavage. Specific antibody binding in RIA assays is determined by measuring the levels of radioactivity bound to the support.

In a competitive immunoassay, the antigen (analyte) in the sample competes with the labeled antigen (tracer) for a limited number of antibody binding sites. The bound antigen is separated from the excess analyte not bound to the antibody. The amount of the analyte in the unknown sample is inversely proportional to the amount of labeled antigen, as measured in a gamma counter or spectrophotometer. Examples of competitive immunoassays include double antibody radioimmunoassays (RIAs), coated tube RIAs and coated well enzyme immunoassays (EIAs). Some examples of solid supports that can be used include plates, tubes, polystyrene beads, nylon, nitrocellulose, cellulose acetate, glass fibers and other types of porous polymers. Suitable labels include radionuclides, fluorophores, chemiluminescent labels, bioluminescent labels, enzymes, for example, as used in ELISA systems, dyes or particles such as colloidal gold or quantum dots.

Assay systems and kits designed to detect one or more specific secretor and Lewis antigens simultaneously are also within the scope of the method. The kits may be dip-stick, flow-through or migratory in design as well as other formats known to those skilled in the art. If desired, the assays can be automated to insure standardization and obtain higher throughput.

FUT2 Activity Assays

FUT2 activity can be measured in a biological sample using any standard method known in the art that is specific for FUT2. For example, a fucosyltransferase assay can be performed in a 20 μl reaction volume containing 3 μM GDP-[$^{14}$C]fucose, 5 mM ATP, 25 mM sodium phosphate, pH 6.0, 40 μg of total protein from cell extracts and phenyl β-D-galactoside or asialofetuin as acceptor substrates. Reaction mixtures are incubated at 37° C. for 2 h, and terminated by the addition of 1 ml of water. The hydrophobic fucosylated phenyl β-D-galactoside products are purified by passing the reaction products through a $C_{18}$ reverse-phase column. Radiolabelled asialofetuin products are purified by filtration through microfiber membranes (GF/C; Whatman) and radioactivity is measured by liquid-scintillation counting. Nanthakumar N N, Dai D, Newburg D S, Walker W A. The role of indigenous microflora in the development of murine intestinal fucosyl- and sialyltransferases. FASEB J (Nov. 15, 2002) 10.1096/fj.02-0031fje (summary: FASEB J 2003; 17:44-6).

FUT2 Genotyping Analysis

FUT2 genotyping can be performed by any standard method known in the art, for example SNP analysis or RT-PCR techniques. SNP's identified as leading to lower levels of FUT2 activity include TRP143TER (428G-A) and ILE129PHE (385A-T). Complete deletion of the FUT2 gene is also observed in some non-secretors. Methods are well know in the art for determining single nucleotide polymorphisms (SNPs), for example: Ahmadian A., Gharizadeh B., Gustafsson A. C., Sterky F., Nyrén P., Uhlén M. and Lundeberg J. *Anal Biochem* 280(1):103-10 (2000); Griffin T. J., Hall J. G., Prudent J. R. and Smith L. M. *Proc Natl Acad Sci USA*

96(11):6301-6 (1999); Nickerson D. A., Kaiser R., Lappin S., Stewart J., Hood L. and Landegren U. *Proc Natl Acad Sci USA* 87(22):8923-7 (1990).

Other Assays

*Ulex europaeus*, a lectin that reacts specifically with alpha-1-fucose, can be used as the basis for detecting secretor antigens, and especially H-2. When *ulex europaeus* conjugated to colloidal gold is exposed to a sample containing secretor antigens under suitable conditions, the *ulex europaeus*-colloidal gold will aggregate thereby producing detectable color change.

Briefly, *ulex europaeus* (UEA1) (Sigma-Aldrich; St Louis, Mo.) is conjugated to colloidal gold after determination of the minimum amount of UEA1 and optimal pH conditions required for stabilization of the colloidal gold. On nitrocellulose strips, 2 µL of the untreated test saliva is added and left to dry for 5 min; 200 µL of casein solution at 1.0% in TBS are added and incubated for 3 min at room temperature. The casein solution is discarded; 150 µL of UEA1-colloidal gold conjugate are added at the optimal dilution in casein solution at 0.05% in TBS, and incubated for 10 min. A detectable color change indicates the presence of secretor antigens in the sample. Control samples are saliva samples known to be H-2 positive or negative.

Methods of Treatment

The methods disclosed herein are also useful for the treatment of an infant at risk for infectious and inflammatory disorders. Treatment can completely or partially abolish some or all of the signs and symptoms of the infectious or inflammatory disorder, decrease the severity of symptoms, delay their onset, or lessen the progression or severity of subsequently developed symptoms.

The methods of treatment are useful for infectious and inflammatory disorders. The methods can be used for full-term infants, premature infants or extremely low birthweight infants. Full term infants include those born between 37 and 42 weeks gestational age; premature infants are typically those born at less than 37 weeks' gestational age. Extremely low birth weight (ELBW) is generally defined as a birth weight less than 1000 g (2 lb, 3 oz). The majority of ELBW infants are also the youngest of premature newborns, usually born at 27 weeks' gestational age or younger. Nearly 1 in 10 infants with low birth weight (<2500 g) are ELBW infants.

The infectious and inflammatory disorders that may be detected using the methods described herein include necrotizing enterocolitis (NEC), gastrointestinal infections, gastrointestinal inflammation, and sepsis. These disorders may be the result of disease, injury or of unknown cause and they may be influenced by one's genetic constitution.

In NEC, portions of the bowel undergo necrosis, i.e., tissue death. Although NEC affects the gastrointestinal tract it can, in severe cases, have profound systemic impact. Initial symptoms may be subtle and can include one or more of: feeding intolerance, delayed gastric emptying, abdominal distention and/or tenderness, ileus/decreased bowel sounds, and, in the advanced stages, abdominal wall erythema and hematochezia Systemic signs are nonspecific and can include any combination of apnea, lethargy, decreased peripheral perfusion, shock (in advanced stages), cardiovascular collapse and bleeding diathesis (consumption coagulopathy). Nonspecific laboratory abnormalities can include the following: hyponatremia, metabolic acidosis, thrombocytopenia, leukopenia or leukocytosis with left shift, neutropenia, prolonged prothrombin time, and activated partial thromboplastin time, decreasing fibrinogen, and rising fibrin split products (in cases of consumption coagulopathy). Although the exact etiology is not known, the etiology may be multifactorial and involve any or all of abnormal bacterial flora, intestinal ischemia and/or reperfusion injury, and intestinal mucosal immaturity.

Gastrointestinal infections in infancy include symptoms of diarrhea; the presence of mucus or blood in stools; vomiting; dehydration; thirst; listlessness; dry mucous membranes; sunken fontanelles; decreased skin turgor; decreased capillary filling time; tachycardia; weak pulse, reduced blood pressure; and tenting or loss of skin turgor. The infectious agents can be bacterial, fungal, viral or parasitic. Examples of bacterial agents include, but are not limited to, *Staphylococcus* spp., *Staphylococcus aureus, Escherichia coli, Streptococcus* spp., *Enterobacter* spp., *Klebsiella* spp., *Bacillus* spp., *Serratia* spp., *Salmonella* spp., *Shigella* spp., *Campylobacter* spp., *Yersinia* spp., and *Clostridium difficile*. Examples of fungal agents include, but are not limited to, *Candida* spp. Examples of parasitic organisms include, but are not limited to, *Cryptosporidium* spp., *Giardia* spp., *Entamoeba histolytica, Cyclospora* spp. Examples of viral organisms include, but are not limited to, rotavirus, cytomegalalovirus, enteric adenovirus, astrovirus, adenoviruses type 40 or 41, Norwalk and other noroviruses, and saporovirus.

The clinical signs of neonatal sepsis are nonspecific and are associated with characteristics of the causative organism and the body's response to the invasion. Neonatal sepsis may be categorized as early or late onset. Eighty-five percent of newborns with early-onset infection present within 24 hours, 5% present at 24-48 hours, and a smaller percentage of patients present between 48 hours and 6 days of life. Onset is most rapid in premature neonates. The infant manifests overt shock with pallor, poor capillary perfusion, and edema. These signs of shock are indicative of severe compromise and are highly associated with mortality. Signs of sepsis can include any or all of cardiac signs, e.g., early stage pulmonary hypertension, decreased cardiac output, hypoxemia, progressive decreases in cardiac output with bradycardia and systemic hypotension; metabolic signs, e.g., hypoglycemia, hyperglycemia, metabolic acidosis, and jaundice; neurologic signs, e.g., meningitis, ventriculitis, arachnoiditis, vasculitis, phlebitis, thrombosis, cerebral edema, infarction, stupor and irritability, impairment of consciousness (i.e., stupor with or without irritability), coma, seizures, bulging anterior fontanel, extensor rigidity, focal cerebral signs, cranial nerve signs, nuchal rigidity, alterations in cerebrospinal fluid (CSF), e.g., an elevated white blood cell count, an elevated protein level, a decreased CSF glucose concentration, and positive culture results. Temperature instability is observed with neonatal sepsis and meningitis, either in response to pyrogens secreted by the bacterial organisms or from sympathetic nervous system instability. The neonate is most likely to be hypothermic. The infant may also have decreased tone, lethargy, and poor feeding. Signs of neurologic hyperactivity are more likely when late-onset meningitis occurs. Other signs of neonatal sepsis include hematologic signs, e.g., thrombocytopenia, abnormal white blood cell counts (WBC), abnormal neutrophil count (PMNs and immature forms), abnormal ratios of immature-to-total neutrophil count, disseminated intravascular coagulation (DIC), abnormalities in prothrombin time (PT), partial thromboplastin time (PTT), and fibrinogen and D-dimer levels; and gastrointestinal signs, e.g., necrotizing enterocolitis.

Organisms that have been implicated in causing late-onset sepsis include coagulase-negative Staphylococci, *S. aureus, E. coli, Klebsiella* spp., *Pseudomonas* spp., *Enterobacter* spp., group B *Streptococcus, Serratia* spp., *Acinetobacter* spp., and *Candida* spp. The infant's skin, respiratory tract, conjunctivae, gastrointestinal tract, and umbilicus may become colonized from the environment, leading to the possibility of late-onset sepsis from invasive microorganisms. Vectors for such colonization may include vascular or urinary catheters, other indwelling lines, or contact from caregivers with bacterial colonization.

Infants identified based on their glycan phenotype (secretor, Lewis, or sialyl antigen expression) as being at risk for infectious and inflammatory disorders, e.g., NEC, gastrointestinal infections, and sepsis, can be treated with therapies that include one or more protective agents. Unless the context indicates otherwise, we use the term "agent" to broadly refer to any substance that affects a target molecule or a target region of the gastrointestinal system in a clinically beneficial way (e.g., to inhibit pathogens from binding to host cell surface glycans). Useful protective agents include, for example, human milk feeding, probiotic organisms, prebiotics, or α1,2 fucosyl glycans.

The α1,2 fucosyl glycans are saccharides that include a fucose terminus in an α1,2 linkage and as such are homologues of secretor antigens, i.e., they include a minimal disaccharide precursor, or core sequence, covalently linked to a fucose residue in an α1,2 configuration. The core sequence can be either the lacto type I structure, galactose (β1-3) N-acetylglucosamine-R, which we abbreviate here as {Gal (β1-3)GlcNAc}-R or the lacto type II structure galactose (β1-4) N-acetylglucosamine-R, which we abbreviate here as{Gal(β1-4)GlcNAc-R}, wherein R is an H, a small radical, or another monosaccharide, disaccharide or polysaccharide or a glycoprotein or glycolipid. These saccharides can be free oligosaccharides or conjugated and expressed as glycoproteins, glycolipids, or other structures. The conjugated and unconjugated forms of oligosaccharides are together classified as glycans. Thus, the α1,2 fucosyl glycans can include 2, 3, 4, 5, 6, 7, 8, 9, 10, 12, 14, 16, 18, 20, 24, 28, 32, 36 or more sugars; one or more of the sugars is covalently linked to a fucose residue in an α1,2 configuration, so that the glycans can include 1, 2, 3, 4, 5, 6, 7, 8, 9, 10, 11, 12, 13, 14, 15, 16, 18 or more fucose residues. Examples of suitable α1,2 fucosyl glycans include, without limitation, 2'-fucosyllactose (2'-FL); lacto-N-fucopentaose-I (LNF-I); lacto-N-difucohexaose I (LDFH I); lactodifucotetraose (LDFT), or such fucosylglycan epitopes attached to a glycolipid, glycopeptide, glycoprotein, mucin, or other scaffold, either in the soluble form or as part of a probiotic organism. The α1,2 fucosyl glycans can be purified from natural sources, e.g., milk, milk products or plant products, using method known to those in the art. Alternatively or in addition, glycans can be synthesized chemically either from naturally occurring precursors or synthetic templates according to methods known in the art. In addition, glycans can be synthesized enzymatically, either in vitro, or in vivo using specifically engineered microorganisms such as bacteria or yeasts, using biosynthetic enzymes well known in the art A protective agent can also be a probiotic organism, i.e., a living microorganism that, when ingested by the host, can modify intestinal microbial populations in a way that benefits the host. Probiotic organisms may provide an increased barrier to translocation of bacteria and bacterial products across mucosa, competitively exclude potential pathogens, modify of host response to microbial products, and enhance enteral nutrition in ways that inhibits the growth of pathogens such as *Klebsiella pneumoniae, Escherichia coli*, and *Candida albicans*.

Probiotic organisms generally include bacteria and yeast. The species of probiotic organism can vary, but suitable species for infants include *Lactobacilli*, e.g., *Lactobacillus rhamnosus* GG, *L. acidophilus, L. casei, L. plantarum, L. reuteri*; and Bifidobacteria, e.g., *Bifidobacterium infantis, B. bifidum, B. breve, B. animalis* subsp. *lactis, B. longum*, as well as *Streptococcus thermophilus*. Useful yeast species include *Saccharomyces boulardii* and *Kluyveromyces lactis*. Probiotic organisms may be either naturally occurring or they may be engineered, i.e., organisms may be provided with genes that enable them to acquire desirable properties such as, but not limited to, the ability to express secretor antigens. Probiotic organisms may be administered separately or in combination. Commercially available probiotic formulations include, for example, Infloran® (Istituto Sieroterapico Berna, Como, Italy) which contains *Lactobacillus acidophilus/Bifidobacterium infantis*; ABC Dophilus (Solgar, Israel) which contains *Bifidobacterium infantis, B. bifidum* and *Streptococcus* thermophilus; and Dicoflor (Vitis Pharma, Warsaw, Poland) which contains *L. rhamnosus* GG. A protective agent can also be a prebiotic, i.e., a non-digestible food ingredient that beneficially affects the host by selectively stimulating the growth and/or the activity of one or a limited number of bacteria in the colon. In contrast to a probiotic, which introduces exogenous bacteria into the colonic microbiota, a prebiotic stimulates the growth of one or a limited number of the potentially health-promoting indigenous microorganisms e.g., Bifidobacteria or Lactobacteria. Examples of prebiotics include fructo-oligosaccharides, e.g., inulin, xylooligosaccharides and galacto-oligosaccharides. Prebiotics can be isolated from natural sources e.g., chicory roots, soybeans, Jerusalem artichokes, beans, onions, garlic, oats, wheat and barley.

One useful prebiotic is inulin, a type of fructan (polymer of fructose). Inulin-type fructans are composed of β-D-fructofuranoses attached by β-2,1 linkages. The first monomer of the chain is either a β-D-glucopyranosyl or β-D-fructopyranosyl residue. Various forms of inulin and inulin fragments are available from commercial sources, e.g., inulin with a degree of polymerization (DP) from 2 to 60 is extracted from chicory roots (Raftiline; Orafti, Tienen, Belgium); oligofructose, which is produced by partial enzymatic hydrolysis of inulin, has a DP<10 (Raftilose; Orafti) and the inulin from which the small-molecular-weight oligomers have been eliminated is called high-performance inulin (Raftiline H P; Orafti). With the use of sucrose as a substrate and a 1,2-β fructan in a fructosyltransferase-catalyzed reaction, a synthetic low-molecular-weight fructan is produced that has a DP<4 (Neosugar or Actilight; Beghin-Meji Industries, Paris).

Protective agents may be administered directly to a patient, either singly or in combination. Generally, the protective agents can be suspended in a pharmaceutically acceptable carrier (e.g., physiological saline or a buffered saline solution) to facilitate their delivery. Encapsulation of the protective agents in a suitable delivery vehicle (e.g., polymeric microparticles or implantable devices) may increase the efficiency of delivery. A composition can be made by combining any of the protective agents provided herein with a pharmaceutically acceptable carrier. Such carriers can include, without limitation, sterile aqueous or non-aqueous solutions, suspensions, and emulsions. Examples of non-aqueous solvents include mineral oil, propylene glycol, polyethylene glycol, vegetable oils, and injectable organic esters. Aqueous carriers include, without limitation, water, alcohol, saline, and buffered solutions. Preservatives, flavorings, and other additives such as, for example, antimicrobials, anti-oxidants (e.g., propyl gallate), chelating agents, inert gases, and the like may also be present. It will be appreciated that any material described herein that is to be administered to a mammal can contain one or more pharmaceutically acceptable carriers.

Alternatively, or in addition, protective agents may be combined with an infant's food source, e.g., expressed breast milk or commercially available infant formula. Any composition described herein can be administered to any part of the host's body for subsequent delivery to the gastrointestinal tract. A composition can be delivered to, for example, the mouth, nasal mucosa, blood, lungs, intestines, muscle tissues, skin, or the peritoneal cavity of a mammal. In terms of routes of delivery, a composition can be administered by intravenous, intracranial, intraperitoneal, intramuscular, subcutaneous, intramuscular, intrarectal, intravaginal, intratracheal, intradermal, or transdermal injection, by oral or nasal administration, or by gradual perfusion over time. In a further example, an aerosol preparation of a composition can be given to a host by inhalation.

The dosage of protective agent that is required will depend on the nature of the agent, route of administration, the nature of the formulation, the nature of the patient's illness, the patient's size, weight, surface area, age, and sex, other drugs being administered, and the judgment of the attending clinician. Wide variations in the needed dosage are to be expected in view of the variety of protective agents and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-times, or more). Encapsulation of the protective agents in a suitable delivery vehicle (e.g., polymeric microparticles) may increase the efficiency of delivery.

The duration of treatment with any composition provided herein can be any length of time from as short as one day to as long as the increased risk might be suspected clinically, for example, through the period of neonatal intensive care unit stay or through infancy. For example, a protective agent can be administered several times per day, once a day, or once a week (for, for example, 4 weeks to several months). It is also noted that the frequency of treatment can be variable. For example, the protective agents can be administered once (or twice, three times, etc.) daily, weekly, or monthly.

An effective amount of any composition provided herein can be administered to an individual at risk of disease or in need of treatment. The term "effective" as used herein refers to any amount that induces a desired response while not inducing significant toxicity in the patient. Such an amount can be determined by assessing a patient's response after administration of a known amount of a particular composition. In addition, the level of toxicity, if any, can be determined by assessing a patient's clinical symptoms before and after administering a known amount of a particular composition. It is noted that the effective amount of a particular composition administered to a patient can be adjusted according to a desired outcome as well as the patient's response and level of toxicity. Significant toxicity can vary for each particular patient and depends on multiple factors including, without limitation, the patient's disease state, age, and tolerance to side effects.

The protective agents provided herein can be administered in conjunction with other prophylactic or therapeutic modalities to an individual at risk for an infectious or inflammatory disorder, e.g., NEC, a gastrointestinal infection or sepsis. The protective agents can be given prior to, simultaneously with or after treatment with other agents or regimes. Other treatments can include administration of antibiotics, for example, vancomycin, kanamycin, gentamicin, cefotaxime, clindamycin or metronidazole, enteral administration of IgG and IgA together, amino acid supplementation, the use of platelet-activating factor (PAF) antagonists or PAF-acetylhydrolase administration, polyunsaturated fatty acid administration, epidermal growth factor administration, and antenatal corticosteroids. The protective agents can also be administered along with or in addition to, other feeding regimes, including judicious administration of human milk feeding, infant formula, parenteral fluids, delayed or slow feeding.

Also provided are methods of determining the course of treatment for an infant who has been identified, based on secretor status, as being at risk for NEC or a gastrointestinal infection. The levels of secretor antigens, e.g., $\alpha 1,2$ fucosyl glycans, in the infant's food source can be compared with levels of the same secretor antigens in a reference sample; the levels of secretor antigens in the food source can be classified as reduced or elevated relative to those secretor antigens in a reference sample. Those infants whose secretor status indicates that they are at risk for NEC and gastrointestinal infections and whose food source also contains reduced levels of secretor antigens can be treated with one or more of $\alpha 1,2$ fucosyl glycans, probiotic organisms or prebiotics.

The infant's food source can be breast milk, either from the infant's own mother or a donor source, or a commercial infant formula. The level of one or more secretor antigens can be assayed in human milk and formula e.g., by ELISA, chromatography or another method and compared to those in a reference sample as described above.

Human milk oligosaccharides typically contain a lactose moiety at the reducing end and a fucose at the nonreducing end. The addition of fucose to an oligosaccharide by an $\alpha 1,2$ linkage is catalyzed primarily by the fucosyltransferase produced by the secretor gene, Se (FUT2); the addition of fucose by an $\alpha 1,3$ or $\alpha 1,4$ linkage is catalyzed by fucosyltransferases produced by the Lewis gene, Le (FUT3) or other $\alpha 1,3$ transferase genes (FUT4, 5, 6, 7, and 9) of this family. Variation in the activities of the 2- and 3/4-fucosyltransferases can result from inactive or partially active genetic polymorphisms. Such variation can produce milk phenotypes that vary in relative quantities of specific fucosyloligosaccharides. Women who are nonsecretors do not express measurable 2-linked fucosyloligosaccharides in their milk or other bodily fluids. However, the expression of milk fucosyloligosaccharides can vary even among secretors and the ratio of 1,2-linked fucosyloligosaccharides to those that contain only 1,3- and 1,4-linked fucose declines exponentially over the first year of lactation.

Examples of suitable $\alpha 1,2$ fucosyl glycans include, without limitation, 2'-fucosyllactose (2'-FL), which is homologous to H-2; lacto-N-fucopentaose-I (LNF-I), which is homologous to H-1; lacto-N-difucohexaose I (LDFH I), which is homologous to Lewis$^b$; lactodifucotetraose (LDFT), which is homologous to Lewis$^y$, as well as lacto-N-difucohexaose II (LNF-II), which is homologous to Lewis$^a$; and lacto-N-difucohexaose III (LNF-III), which is homologous to Lewis$^x$. The core type 1 structure, lacto-N-tetraose (LNT), is a terminal Gal$\beta$1,3GlcNAc on lactose. Lactose is the core for the most abundant type 2 structures in milk (2'-FL, 3-FL, and LDFT), whereas lacto-N-neotetraose, Gal$\beta$1,4GlcNAc on a lactose terminus, is the core for LNF-III. In other tissues, Lewis structural moieties are based on a lactosamine backbone (Gal-GlcNAc); however, the most prevalent type 2 fucosyloligosaccharides in human milk are synthesized from lactose (Gal-Glc) and therefore are defined as the glucose analogs to the type 2 Lewis structures. The epitopes of these structures can also be found expressed in various glycoconjugates of milk, and these glycoconjugates may be used for prophylactic and/or therapeutic purposes.

Infants whose food supply contains a reduced level of secretor antigens may be supplemented enterally by feeding α1,2 fucosyl glycans, probiotic organisms or prebiotics as described above.

EXAMPLES

Example 1

Bacterial Colonization Induces Change in Intestinal Glycoylation

Expression of fucosylated and sialylated glycans in gut change during development, reminiscent of the changes seen in milk over the course of lactation. In the mouse small intestine, Fut2 mRNA and α1,2/3-fucosyltransferase activity increase abruptly at weaning, while expression of sialyltransferase activity decreases. The inversion of these two enzyme activities coincides with an abrupt change of mucosal glycan expression at weaning and a change in composition of gut microbiota. Whether induction of these changes was through an intrinsic genetic program, or by exogenous control by diet or adult microflora, was tested as described below.

The upregulation of fucosyltransferase that normally would occur at weaning does not occur in germ-free mice. However, whenever post-weaning germ-free mice are colonized, fucosyltransferase and fucosylation are induced. This suggested that bacterial colonization was inducing fucosylation of the mucosal surface. This was confirmed in mature mice that were depleted of bacteria (BD) by drinking a mixture of antibiotics. After two weeks, Fut2 mRNA and fucosyltransferase activity dropped to the levels seen in germ-free mice, and fucosylglycans (*Ulex europaeus* agglutinin 1 [UEA-1] staining) were no longer expressed in the colon. Cessation of antibiotic treatment and repletion with normal microbiota (XBD) caused a recovery of Fut2 mRNA and fucosyltransferase activity to levels of normally colonized mature gut, and full expression of fucosylglycans on the mucosal surface. This confirmed that fucosylation of the gut is controlled by its colonization.

It was hypothesized that the mechanism whereby extracellular colonization results in the intracellular activation of the ERK and JNK pathway involves undefined transmembrane receptors. A family of transmembrane receptors, the toll-like receptors (TLR), were already known to sense the extracellular presence of pattern recognition molecules unique to microbes and transmit signals to the nucleus through transcellular signal transduction pathways. Accordingly, we tested whether one of the TLR family members might be responsible for the communication between the bacteria and the gut mucosa that results in bacterial-induced Fut2 mRNA and fucosyltransferase activity in the colonic mucosa. Like wild-type mice, mice with mutations in TLR2 are able to express normal fucosylation that is lost with a loss of colonization (FIG. 12, next page). In contrast, mutants of TLR4 or its downstream mediator, MyD88, do not express the full level of fucosylation, and this fucosylation is not affected by loss of colonization. This is consistent with the TLR4 signaling pathway being necessary for bacteria-induced mucosal fucosylation. To test whether activation of TLR4 per se in bacteria-depleted mice is sufficient to activate the transduction pathways that stimulate Fut2 expression, the specific ligand for TLR4, LPS, was administered in drinking water to bacteria-depleted mice. Fucosyltransferase activity and Fut2 mRNA of the BD mouse colon recovers to normal adult levels when treated with ultra-pure LPS. In contrast, in BD mice treated with peptidoglycan (PG), the ligand for TLR2, the level of fucosyltransferase activity and Fut2 mRNA remains at the lower levels of BD mice. These data strongly suggest that binding and stimulation of TLR4 in bacterially depleted mice is the critical signal that is both necessary and sufficient for adult gut microbiota to signal the epithelial nuclear events that result in fucosylation of the gut.

If binding to fucosylated TLR4 is the essential signal for the colonization-induced mucosal fucosylation, the subset of the microbiota that bind to fucose would be expected to recapitulate this phenomenon. This hypothesis was tested with a fucose-utilizing species of the mixed microbiota. *Bacteroides fragilis* is a specific fucose-utilizing bacterium found in typical mature mammalian microbiota. Monocolonization of bacterially depleted mice with *B. fragilis* induced fucosylation to the same extent as recolonization with mixed microbiota, mediated through induced Fut2 mRNA, consistent with the fucose-utilizing bacteria of the mixed microbiota being responsible for the induction of fucose expression. If this were so, a mutant *B. fragilis* made incapable of utilizing fucose would be expected to lose the ability to signal the induction of fucosylation in the mucosa, as observed in the right panel. Thus, binding to one set of fucosylated epitopes, seemingly fucosylated TLR4, in bacterially depleted mice by fucose-utilizing bacteria seems to be sufficient for the induction of the fucosylated phenotype on the intestinal mucosa.

Example 2

Histo-blood Group Antigens (Glycans) in Saliva of Hospitalized Infants

Thirty-six infants hospitalized in Cincinnati area Newborn Intensive Care Units between 24 and 42 weeks gestational age (GA) were enrolled between May and December 2005. Twelve subjects per group were stratified by gestational age into three groups, 24 to 28 weeks, 29 to 32 weeks, and greater than or equal to 33 weeks gestational age at birth. Infants diagnosed with major congenital anomalies were excluded. Institutional Review Boards at Cincinnati Children's Hospital Medical Center, Good Samaritan Hospital, and University Hospital approved the study. Informed written consent was obtained from the parents. Maternal demographic information collected included maternal age, race, obstetric history, complications encountered in the current pregnancy, and maternal medications during pregnancy. Clinical and demographic data recorded at enrollment of subjects included race, gender, gestational age, birth weight, length and head circumference. Clinical data recorded on study infants during their hospital course included requirement and duration of respiratory support, initiation and type (human milk or formula) of enteral nutrition, episodes of culture-proven sepsis, occurrence of necrotizing enterocolitis (Bell's stage 2 or greater), and history of antibiotic use.

Specimen collection. Saliva specimens were obtained at enrollment and every two weeks while subjects remained hospitalized. A maximum of five samples were collected from each subject. Saliva specimens were collected one to two hours after feeding by clearing the mouth of residual milk or formula with soft gauze and inserting a sterile cotton swab. Once visibly saturated with saliva, the cotton swab was transferred into a specimen container. Specimens were held briefly at 4° C. then transferred to −80° C. A total of 107 saliva samples were collected. Saliva-saturated cotton swabs were allowed to thaw in 1 ml phosphate buffered saline (PBS) for 5 minutes. The specimens were then centrifuged at 10,000×g for 10 minutes and supernatants were collected. Each specimen was boiled at 100° C. for 10 minutes and placed at 4° C. overnight. Samples were again centrifuged at 10,000 g× for 10 minutes, the supernatants were collected, separated into 100 ml aliquots and placed at −80° C.

Optimal dilutions of saliva samples were determined for each antigen detection assay. Saliva specimens diluted 1:50 were used for detection of $Le^a$, $Le^x$, H-1, H-2, sialyl $Le^a$ and sialyl $Le^x$ antigens. Saliva specimen diluted 1:125 were used for $Le^y$, whereas dilutions of 1:250 were used for $Le^b$ antigen detection. For quantitative analysis of saliva samples from an individual subject, a 1:50 dilution was used for all antigens. Samples were coated onto microtiter plates (Dynex Immunlon) overnight at 4° C. After blocking with 5% Blotto, monoclonal antibodies (MAbs) specific to Lewis and ABH antigens were used at a dilution of 1:100. The following MAbs specific to human histo-blood group antigen types were used for histo-blood group phenotype determinations. MAbs BG-4 anti-H type 1, BG-5 anti-$Le^a$, BG-6 anti-$Le^b$, BG-7 anti-$Le^x$, and BG-8 anti-$Le^y$ were purchased from Signet Laboratories. MAb BCR9031 anti-H type 2, BCR9010 anti-A, and BCRM 11007 anti-B were purchased from Accurate Chemical and Scientific Corporation. MAbs for Sialyl $Le^a$ and $Le^x$ were products of EMD, catalog number 565942 and 565953 respectively. After incubation for 1 hour at 37° C., horseradish peroxidase (HRP) conjugated goat anti-mouse IgG, IgG3 or IgM antibodies were added. After each step, the plates were washed five times with PBS/Tween solution. Colorimetric reactions were detected using a TMB kit (Kirkegard & Perry Laboratories), and read at a wavelength of 450 nm using an EIA spectrum reader (Tecan).

Shown in Table 1 is the average optical density values (±the standard error) obtained by ELISA in study week 1 and prior to discharge for all infants ever found to have a detectable level of that antigen in a saliva sample. Each antigen was considered separately. This analysis indicated that most secretor antigens ($Lewis^b$, $Lewis^y$, and H-2) were present in premature infants from birth, and that secretor antigen expression increased postpartum. As shown in Table 1, levels of secretor antigens (shown in boldface type) were higher in the samples collected at subsequent time points, i.e., those samples taken from infants prior to discharge. Levels of $Lewis^b$, $Lewis^y$ and $Lewis^b$ and $Lewis^y$ showed a statistically significant increase over time; levels of the other secretor antigens, H-1 and H-2, also increased, although the rate of increase did not approach statistical significance.

TABLE 1

Glycan Expression in Saliva of Premature Infants

| Antigen | N | Postpartum Week 1 Saliva Sample* | Pre-Discharge Saliva Sample* | Postpartum change p-value** |
|---|---|---|---|---|
| Secretor | | | | |
| H-1 | 20 | 0.18 (0.08) | 0.29 (0.06) | 0.13 |
| H-2 | 30 | 1.45 (0.20) | 1.80 (0.21) | 0.41 |
| $Lewis^b$ | 28 | 1.92 (0.20) | 4.02 (0.45) | 0.0005 |
| $Lewis^y$ | 31 | 2.78 (0.24) | 3.90 (0.29) | 0.024 |
| Lewis (only) | | | | |
| $Lewis^a$ | 32 | 1.22 (0.46) | 1.27 (0.54) | 0.82 |
| $Lewis^x$ | 26 | 0.71 (0.19) | 0.95 (0.32) | 0.40 |
| Sialyl | | | | |
| $SLe^a$ | 36 | 3.63 (0.61) | 3.10 (0.89) | 0.29 |
| $SLe^x$ | 35 | 1.85 (0.27) | 1.61 (0.36) | 0.49 |

*Values are expressed as the mean optical density; the standard error is in parentheses.
**p-values were determined using a Student's t-test.

Example 3

Antibiotic Use and Glycan Expression Phenotype

The relationship between secretor antigen expression, postpartum age, gestational age and antibiotic use was analyzed using a Generalized Estimating Equation (GEE). Saliva samples were collected from 24 infants in the first week of age postpartum and "prior to discharge". Levels of histo-blood group antigens $Lewis^a$, $Lewis^x$, $Lewis^b$, $Lewis^y$, H-1, H-2, Sialyl-$Lewis^a$ ($SLe^a$) and Sialyl-$Lewis^x$ ($SLe^x$) were measured by ELISA according to the method described in Example 1. Infants were classified according to gestational age at birth into groups of 22-28 weeks, 29-34 weeks, and 35-40 weeks. For GEE analysis, histo-blood group antigen O.D. values were used as dependent variables (designated as "Model" in column 1 of Table 2) and week of age postpartum, gestational age group, and number of days of antibiotic use were included as independent variables. The resulting beta coefficients for the GEE analysis are shown in Table 2. The GEE analysis indicated that the courses (defined as antibiotic treatment of the infant from 1-5 days) was associated with significantly decreased expression of secretor antigens postpartum.

TABLE 2

Beta coefficients (SE) from Generalized Estimating Equation (GEE) analysis: Histoblood group antigen O.D. values (dependent variable) measured in samples from 24 infants with two saliva samples collected at Week 1 and prior to hospital discharge (3-7 weeks after birth). Week of age postpartum, gestational age group, and number of days of antibiotic use were included as independent variables

| Model | Week of age postpartum | Gestational Age Group* | No. of courses of antibiotic use |
|---|---|---|---|
| Lewis b and y (combined O.D. values) | 0.54 (.17)*** | 0.005 (.39) | −0.33 (.37) |
| Sialyl Le X | −0.10 (.08) | −0.17 (0.21) | 0.52 (.14)*** |

*Gestational age groups: 1 = 24-28 wks, 2 = 29-32 wks; 3 = 33-40 wks at birth,
***p ≤ 0.001

Example 4

Extremely Low Birthweight Infant (ELBW) Outcomes Study

Figure 6:
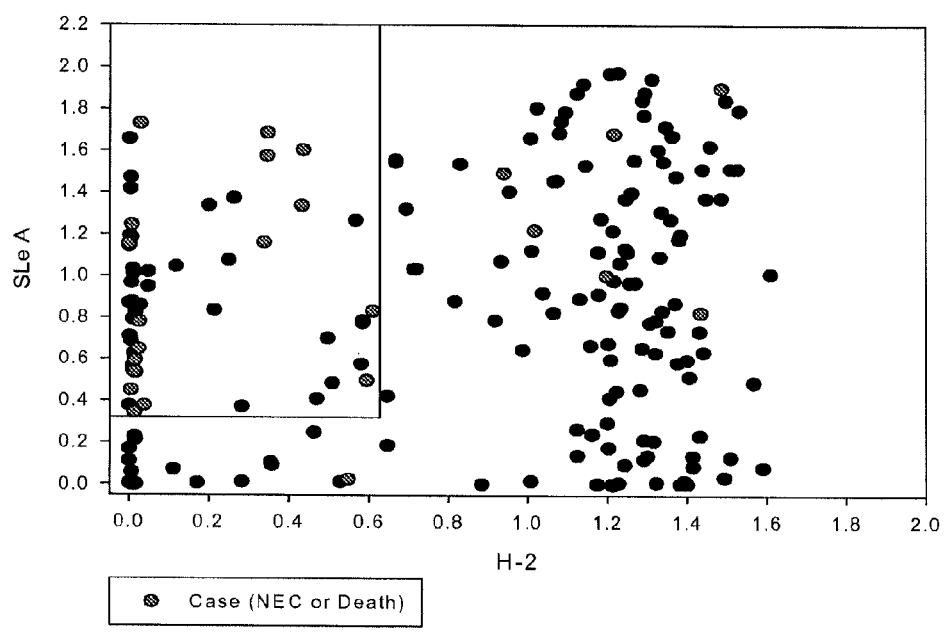
FIG. 6: Scatterplot of H-2 and sLe A antigen optical density (O.D.) values by EIA measured from a saliva sample collected in week 2 (days 8-14) from 192 ELBW (<1000 grams) infants in Cincinnati NICUs; 24 (12.5%) developed NEC or died. The high and low risk sets were systematically identified by CART analysis to minimize misclassification of cases and non-cases. The H-2 cut-point for high risk was identified as an O.D. <0.627 (lowest 38% of values, including non-secretor infants). In the H-2 high risk group, 18 cases occurred in 73 infants (incidence=24.7%) compared to 6 cases in 119 infants (incidence=5.0%; relative risk [RR]=4.9, 95% confidence interval [CI]=2.0 to 11.8, P<0.0001). The sLe$^a$ cutpoint for high risk was identified as an O.D. >0.318 (highest 76% of values). The infants in both high risk groups (defined by low H-2 and high sLe$^a$ O.D. values) creates the high risk set indicated in the figure of 17 cases in 54 infants (incidence=31.5%) compared to all other infants combined, who define the low risk set, which comprises 7 cases in 138 infants (incidence=5.1%). This combined classification resulted in a highly significant split of high vs. low risk (RR=6.2, 95% CI 2.7 to 14.1, P<0.0001).

The relationship between secretor antigen expression, clinical outcome and necrotizing enterocolitis (NEC) was analyzed in a cohort of 192 extremely low birthweight (<1000 gram) infants seen in Cincinnati neonatal intensive care units, with saliva samples collected in week 1 (days 1-7) and week 2 (days 8-14) after birth. This was a prospective study conducted at three hospitals that provide level III neonatal intensive care within the Cincinnati region, with infants enrolled between 2002-2004. Exclusion criteria included the presence of major chromosomal or congenital anomalies, diagnosis of cystic fibrosis, or a medical condition judged by the attending neonatologist to be incompatible with survival beyond the first week of life. After enrollment, a saliva sample was obtained along with demographic and clinical data. Infants were followed with once-weekly saliva sample collections. Saliva was collected with sterile cotton-tipped swabs placed in the mouth of the infant and saturated with saliva, by nursing or research staff between 5:00 am and 10:00 am before feeding. Samples were frozen at −80 C. Saliva was extracted from the swab by removing the cotton portion of the swab, placing it in a 1 mL syringe, and eluting the contents with 250 mL of normal saline. FIG. 6 is a scatter plot of the results.

The rate of NEC in the study population was 7.8% (n=15); the rate of late onset sepsis was 34.9% (n=67); the rate of death was 9.3% (n=18). Of the 15 NEC cases, there was a 60% case fatality and the rate of death due to NEC among the 192 infants studied was 4.7% (n=9).

Levels of histo-blood group antigens Lewis$^a$, Lewis$_x$, Lewis$^b$, Lewis$^y$, H1, H2, Sialyl-Lewis$^a$ (SLe$^a$) and Sialyl-Lewis$^x$ (SLe$^x$) were measured by ELISA according to the method described in Example 1 in a single banked saliva sample taken from each infant. Individuals expressing one or more antigens containing an α1,2-linked fucose were designated as secretors. Twenty percent (20%), i.e., 39 infants, were classified as non-secretors (no detectable secretor antigen); 153 infants (80%) were classified as secretors.

Figure 2A:
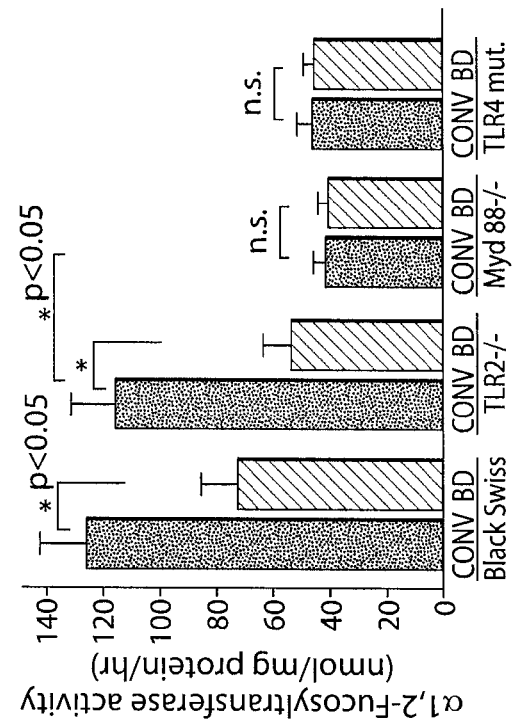
Figure 3:
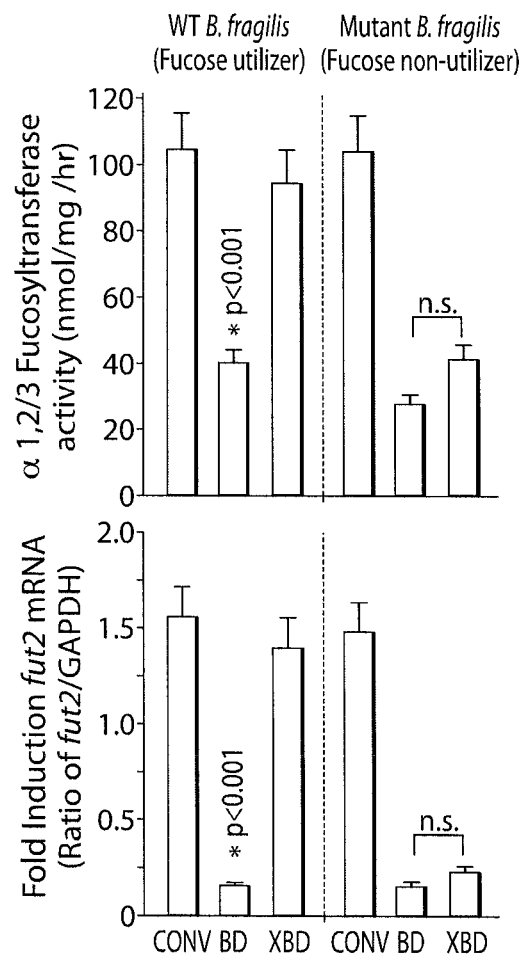
FIG. 3: Monocolonization by *B. fragilis* induces intestinal fucosylation.
Figure 4:
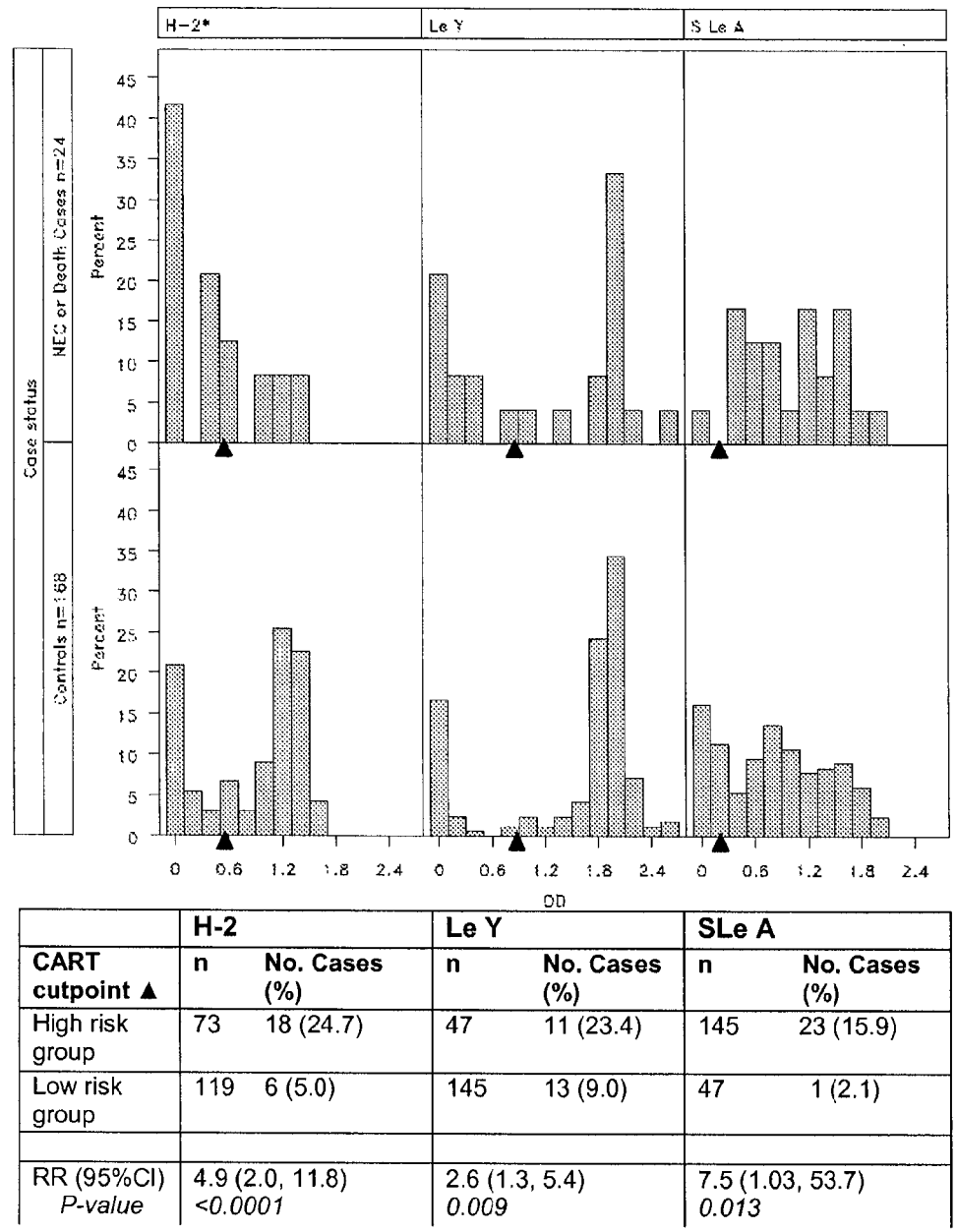
FIG. 4: Histograms indicate the distribution of H-2, Le y, and sLe a antigens measured in saliva as optical density (O.D.) values comparing 24 cases of NEC or death (top row) and 168 controls (bottom row). Samples were collected at 8-14 days (week 2). The table indicates the incidence of NEC or death, the relative risk and p-value comparing the risk groups identified by CART analysis. The triangle symbol indicates the cutpoint in continuous values of each antigen identified by CART analysis to optimally distinguish between a high and low risk group (node). This cutpoint is applied in the table for each antigen. For H-2 only: the O.D. value distribution differs significantly (P=0.004, Wilcoxon Mann Whitney test) comparing NEC and death cases with controls.

Classification and Regression Tree (CART) analysis was used to identify the high-risk subgroups for NEC or death using the glycan (secretor, Lewis, and sialyl antigen) values of each individual. CART analysis is an established statistical method that uses tree-based partitioning to identify algorithms for diagnostic or prognostic markers of risk in clinical studies such as this. An empirical statistical technique based on recursive partitioning analysis, the method does not require parametric assumptions, and involves the segregation of different values of continuous or categorical data through a decision tree composed of progressive binary splits. Every value of each predictor variable is considered a potential split, and the optimal split is selected based on minimizing misclassification of cases and non-cases using an "impurity criterion", which is the reduction in the residual sum of squares that would occur with a binary split of the data at that node. All seven antigens were analyzed, one at a time, using CART to generate the optimal cut-point for each variable. The categorical variables created from that step (partially shown in FIG. 1) were then re-entered into a second CART model. In this step, H-2 emerged as the first split (see FIG. 2), defining 73 infants into a high risk group at the lowest 38$^{th}$ percentile of values and below (O.D. value <0.627). This group had 18 cases of NEC or death (incidence 24.7%) compared with 6 cases of NEC or death among the 119 infants classified into the H-2 low-risk group (incidence 5.0%, P<0.0001). Among the 73 infants classified into the high-risk group by their salivary H-2 (the "low-secretors" and non-secretors), a second split occurred in the CART model: 19 were identified as low-risk (1 case of NEC or death, incidence 5.2%) and 54 were identified as high risk (17 cases of NEC or death, incidence 31.5%). This model identified one high-risk group (the low- and non-secretors, 31.5% risk) and two low-risk groups (the 119 who were high secretors and the 19 who were non- and low-secretors but also low sLe$^a$) with nearly identical risk approaching 5%. Lastly, these 3 nodes were re-entered into the final CART model: the result was a binary split identifying the high-risk group vs. all others (FIGS. 2 and 3). This single split, combining H-2 and sLe$^a$ predictive high-risk cut-points, was found by receiver operating curve area under the curve analysis to have an overall predictive value of 77. The CART analysis is summarized in FIGS. 5 and 6.

A number of embodiments of the invention have been described. Nevertheless, it will be understood that various modifications may be made without departing from the spirit and scope of the invention.

What is claimed:

1. A method for treating necrotizing enterocolitis (NEC), the method comprising:
    administering to an infant having NEC an effective amount of a composition comprising one or more alpha-1,2 fucosyl glycans,
    wherein the infant is a premature infant or an infant having a birth weight of less than 2500 grams, and
    wherein the one or more alpha-1,2 fucosyl glycans are either purified from a natural source or chemically synthesized.

2. The method of claim 1, wherein the one or more alpha-1,2 fucosyl glycans each include a fucose terminus in an α1,2-linkage to a core sequence, which is Gal(β1-3)GlcNAc-$R_1$ or Gal(β1-3)GlcNAc-$R_2$, each of $R_1$ and $R_2$ independently being H, a small radical, a monosaccharide, a disaccharide, or a polysaccharide.

3. The method of claim 2, wherein the one or more alpha-1,2 fucosyl glycans are selected from the group consisting of 2'-fucosyllactose (2'-FL), lacto-N-fucopentaose-I (LNF-I), lacto-N-difucohexaose I (LDFH I), and lactodifucotetraose (LDFT).

4. The method of claim 1, wherein the one or more alpha-1,2 fucosyl glycans are conjugated to a scaffold.

5. The method of claim 4, wherein the scaffold is a glycoprotein, a glycopeptide, a glycolipid, or a mucin.

6. The method of claim 1, wherein the composition further comprises one or more probiotic organisms.

7. The method of claim 6, wherein the one or more probiotic organisms are selected from the group consisting of *Lactobacilli rhamnosus* GG, *Lactobacilli acidophilus*, *Lactobacilli casiei*, *Lactobacilli plantarum*, *Lactobacilli reuteri*, *Bifidobacterium infantis*, *Bifidobacterium bifidum*, *Bifidobacterium Breve*, *Bifidobacterium animalis lactis*, *Bifidobacterium longum*, *Streptococcus thermophiles*, *Saccharomyces boulardii*, and *Kluyveromyces lactis*.

8. The method of claim 1, wherein the composition further comprises one or more prebiotics.

9. The method of claim 8, wherein the one or more prebiotics are fructo-oligosaccharides.

10. The method of claim 9, wherein the fructo-oligosaccharides are inulin, xylooligosaccharides, or galactooligosaccharides.

11. The method of claim 1, wherein the composition further comprises a pharmaceutically acceptable carrier.

12. The method of claim 1, wherein the composition is administered to the infant multiple times per day, once per day, or once per week.

13. The method of claim 1, wherein the composition is administered to the infant for at least 4 weeks.

14. The method of claim 1, wherein the composition is administered orally.

15. The method of claim 1, wherein the composition is administered orally to the infant multiple times per day, once per day, or once per week for at least 4 weeks.

16. The method of claim 1, wherein the premature infant is an infant who is born at less than 37 weeks gestational age.

17. The method of claim 1, wherein the infant has a birth weight of less than 1000 grams.

18. A method for treating a gastrointestinal infectious or gastrointestinal inflammatory disorder, the method comprising:
    administering to an infant having a gastrointestinal infectious or gastrointestinal inflammatory disorder an effective amount of a composition comprising one or more alpha-1,2 fucosyl glycans,
    wherein the infant is a premature infant or an infant having a birth weight of less than 2500 grams,
    wherein the one or more alpha-1,2 fucosyl glycans are either purified from a natural source or chemically synthesized, and
    wherein if the infant has a gastrointestinal infectious disorder, the infant does not have diarrhea.

19. The method of claim 18, wherein the one or more alpha-1,2 fucosyl glycans each include a fucose terminus in an α1,2-linkage to a core sequence, which is Gal(β1-3)GlcNAc-$R_1$ or Gal(β1-3)GlcNAc-$R_2$, each of $R_1$ and $R_2$ independently being H, a small radical, a monosaccharide, a disaccharide, or a polysaccharide.

20. The method of claim 19, wherein the one or more alpha-1,2 fucosyl glycans are selected from the group consisting of 2'-fucosyllactose (2'-FL), lacto-N-fucopentaose-I (LNF-I), lacto-N-difucohexaose I (LDFH I), and lactodifucotetraose (LDFT).

21. The method of claim 18, wherein the composition further comprises one or more probiotic organisms.

22. The method of claim 18, wherein the composition further comprises one or more prebiotics.

23. The method of claim 18, wherein the premature infant is an infant who is born at less than 37 weeks gestational age.

24. The method of claim 18, wherein the infant has a birth weight of less than 1000 grams.

25. The method of claim 18, wherein the gastrointestinal infectious or gastrointestinal inflammatory disorder is selected from the group consisting of necrotizing enterocolitis (NEC), a gastrointestinal infection, gastrointestinal inflammation, and sepsis.

26. The method of claim 18, wherein the infant has a gastrointestinal inflammatory disorder.

* * * * *

SEQUENCE LISTING

<160> NUMBER OF SEQ ID NOS: 2

<210> SEQ ID NO 1
<211> LENGTH: 3115
<212> TYPE: DNA
<213> ORGANISM: Homo sapiens

<400> SEQUENCE: 1

```
agtcaccgat gctggaaggg tttctttggc cctgagtgaa gagagaccca gagggaacac      60
tgaggtgcct gcccaaccac tctgtcccgg tttccttcag caggaccagg tgagagaagc     120
catgctggtc gttcagatgc ctttctcctt tcccatggcc cacttcatcc tctttgtctt     180
tacggtttcc actatatttc acgttcagca gcggctagcg aagattcaag ccatgtggga     240
gttaccggtg cagataccag tgctagcctc aacatcaaag gcactgggac ccagccagct     300 caggggatg tggacgatca atgcaatagg ccgcctgggg aaccagatgg gcgagtacgc      360
cacactgtac gccctggcca agatgaacgg gcggcccgcc ttcatcccgg cccagatgca     420
cagcaccctg gcccccatct tcagaatcac cctgccggtg ctgcacagcg ccacggccag     480
caggatcccc tggcagaact accacctgaa cgactggatg gaggaggaat accgccacat     540
cccgggggag tacgtccgct tcaccggcta ccctgctcc tggaccttct accaccacct     600
ccgccaggag atcctccagg agttcaccct gcacgaccac gtgcgggagg aggcccgaaa     660
gttcctgcgg ggcctgcagg tgaacgggag ccggccgggc acctttgtag gggtccatgt     720
tcgccgaggg gactatgtcc atgtcatgcc aaaagtgtgg aagggggtgg tggccgaccg     780
gcgataccta cagcaggccc tggactggtt ccgagctcgc tacagctccc tcatcttcgt     840
```

```
ggtcaccagt aatggcatgg cctggtgtcg ggagaacatt gacacctccc acggtgatgt   900
ggtgtttgct ggcgatggca ttgagggctc acctgccaaa gattttgctc tactcacaca   960
gtgtaaccac accatcatga ccattgggac gttcgggatc tgggccgcat acctcacggg  1020
cggagacacc atctacctgg ccaattacac cctccccgac tccccttttcc tcaaaatctt  1080
taagccagag gcagccttcc tgccggagtg gacagggatt gccgcagacc tgtccccctt  1140
actcaagcac taatgctggc ccattctttg agacctttc tccttctctg cctccctcaa  1200
gatgagtgcc cgggcatgag aagcacatgg ttccatgagc aggacccatc tctcttctgt  1260
gaagatgcgt tgggctgcaa gtaacagaaa tctcagtgaa cagtggcctg cgtggtggc   1320
tcatgcctgt aatgctcgca ctttgtgagg ccagggtggg tggatcactt gaggtcagga  1380
gttcaagact agcctggcca acatggtgaa accccatctc gactaaaaat acaaaaatta  1440
gccaggcgtg gtggtgcaca cctgtaatcc cagctactcg ggaggctgag gcaagagaat  1500
cacttgaacc caggaggcgg aggttgcagt gagccaagat ggtgccgctg cactccagtc  1560
tgggtgacac agcaagactc catctcaaaa aaaaaaaaaa aaaaagaaa agaaaaagaa   1620
atgaatgggt tcaaagacca taatcatgca tatcacataa gaccagaagt ggcccaggtc  1680
cagggtcagt taatttagcg gctccacaaa gtcatcagtc acctgagctc catccatctt  1740
cacatgctgt gctaccattt cttagctgta tcatcccatg gtcccaaaag ggctgctaca  1800
catccagcca tcacatgcag ataattcctt tcaaaaacag cagaaagagg ctcgttcttg  1860
tcttggtccc ttttgaagaa tgaatgaaac cttcctaagc cttccagcaa tttccccca   1920
actccgatgg gtaggaattg tcacatacc atgtgacccg ataggaggca aaagaaatga   1980
gacttctggg attagtttag cctcagattc tgcagctgag aagttgatca gccacctctg  2040
aaggacatgc agcttgcaga aaattagggt ggtgttacca aggtgaaaag gggaaatggc  2100
tttagagtag acaacagaga tgccctgagg ggttgtgtag gttgttcact gcaggaagtc  2160
ccctggttaa gaaggcaagt gggggtttaaa cagacccaca gtctactcat caaaccaggt  2220
gtccttggca ttgtgtccac ccagagagct cactgttttc ttttctttt cttttctttt   2280
tttttttttt tttgagatgg agtcttgctg catcccccag gctggagtgc agtggcatga  2340
tcttggctca ctgcagcctc cgcctcccag gttcaagcga ttctcctgcc tcagcctccc  2400
gagtagctag gattacaggt gcgtgccacc acgcccagct aattttttata tgtttagtgg  2460
aaatggagtt tcaccatgtt ggtcaggctg gtctcaaact cctgacctca tgatccgcct  2520
tcctcggcct cccaaagtgc tgggattaca ggtgttagcc actgcgcccg gcccctagagc  2580
tcactgtttt ctagttagtc catctggaag tggagccttt ttccagtttg cacaaatgtg  2640
ccatattggc ttgtagctgg catgcatcca agtccatagg tcctgcctct tcaatcctgg  2700
cttttctaggg cctgggatga tcattgctag aactgagaga ccagcctggc tcagtgaact  2760
tcagggcgtt ccgttcattc tttcagtaaa tgtttgcagc acatgtgtta catgtcaggc  2820
agtgaaaccc cccacagcag ccttccctct cagaggatac atttgtaacc attacacagt  2880
catcaaagga ataatttttt ttaatcacca gtgtgcatac agtcatggag ttgggtattc  2940
ccagctacca gggaggctga ggtgggagga ttgcttgatg ccaggagtta gggaatatag  3000
tgcaccgtga ttggacttgc gaatagccac tgcactgcgg cctggacgac gtagtgatac  3060
cctgactctt ataaataaat aaatgaataa acacaattat gactttgcgg atggg        3115
```

<210> SEQ ID NO 2
<211> LENGTH: 343

<212> TYPE: PRT
<213> ORGANISM: Homo sapiens

<400> SEQUENCE: 2

Met Leu Val Val Gln Met Pro Phe Ser Phe Pro Met Ala His Phe Ile
 1               5                  10                  15

Leu Phe Val Phe Thr Val Ser Thr Ile Phe His Val Gln Gln Arg Leu
            20                  25                  30

Ala Lys Ile Gln Ala Met Trp Glu Leu Pro Val Gln Ile Pro Val Leu
        35                  40                  45

Ala Ser Thr Ser Lys Ala Leu Gly Pro Ser Gln Leu Arg Gly Met Trp
    50                  55                  60

Thr Ile Asn Ala Ile Gly Arg Leu Gly Asn Gln Met Gly Glu Tyr Ala
65                  70                  75                  80

Thr Leu Tyr Ala Leu Ala Lys Met Asn Gly Arg Pro Ala Phe Ile Pro
                85                  90                  95

Ala Gln Met His Ser Thr Leu Ala Pro Ile Phe Arg Ile Thr Leu Pro
            100                 105                 110

Val Leu His Ser Ala Thr Ala Ser Arg Ile Pro Trp Gln Asn Tyr His
        115                 120                 125

Leu Asn Asp Trp Met Glu Glu Tyr Arg His Ile Pro Gly Glu Tyr
    130                 135                 140

Val Arg Phe Thr Gly Tyr Pro Cys Ser Trp Thr Phe Tyr His His Leu
145                 150                 155                 160

Arg Gln Glu Ile Leu Gln Glu Phe Thr Leu His Asp His Val Arg Glu
                165                 170                 175

Glu Ala Gln Lys Phe Leu Arg Gly Leu Gln Val Asn Gly Ser Arg Pro
            180                 185                 190

Gly Thr Phe Val Gly Val His Val Arg Arg Gly Asp Tyr Val His Val
        195                 200                 205

Met Pro Lys Val Trp Lys Gly Val Val Ala Asp Arg Arg Tyr Leu Gln
    210                 215                 220

Gln Ala Leu Asp Trp Phe Arg Ala Arg Tyr Ser Ser Leu Ile Phe Val
225                 230                 235                 240

Val Thr Ser Asn Gly Met Ala Trp Cys Arg Glu Asn Ile Asp Thr Ser
                245                 250                 255

His Gly Asp Val Val Phe Ala Gly Asp Gly Ile Glu Gly Ser Pro Ala
            260                 265                 270

Lys Asp Phe Ala Leu Leu Thr Gln Cys Asn His Thr Ile Met Thr Ile
        275                 280                 285

Gly Thr Phe Gly Ile Trp Ala Ala Tyr Leu Thr Gly Gly Asp Thr Ile
    290                 295                 300

Tyr Leu Ala Asn Tyr Thr Leu Pro Asp Ser Pro Phe Leu Lys Ile Phe
305                 310                 315                 320

Lys Pro Glu Ala Ala Phe Leu Pro Glu Trp Thr Gly Ile Ala Ala Asp
                325                 330                 335

Leu Ser Pro Leu Leu Lys His
            340